(12) United States Patent
Takaiwa et al.

(10) Patent No.: US 6,759,228 B2
(45) Date of Patent: *Jul. 6, 2004

(54) ALKALINE PROTEASE

(75) Inventors: Mikio Takaiwa, Tochigi (JP); Mitsuyoshi Okuda, Tochigi (JP); Katsuhisa Saeki, Tochigi (JP); Hiromi Kubota, Tochigi (JP); Jun Hitomi, Tochigi (JP); Yasushi Kageyama, Tochigi (JP); Shitsuw Shikata, Wakayama (JP); Masafumi Nomura, Wakayama (JP)

(73) Assignee: Kao Corporation, Tokyo (JP)

( * ) Notice: Subject to any disclaimer, the term of this patent is extended or adjusted under 35 U.S.C. 154(b) by 118 days.

This patent is subject to a terminal disclaimer.

(21) Appl. No.: 09/920,954

(22) Filed: Aug. 3, 2001

(65) Prior Publication Data

US 2002/0064854 A1 May 30, 2002

Related U.S. Application Data

(63) Continuation of application No. 09/509,814, filed as application No. PCT/JP98/04528 on Oct. 7, 1997, now Pat. No. 6,376,227.

(30) Foreign Application Priority Data

Oct. 7, 1997 (JP) ............................................. 9-274570

(51) Int. Cl.⁷ .............................. C12N 9/52; C11D 3/00; C11D 2/42
(52) U.S. Cl. ....................... 435/220; 435/69.1; 435/183; 435/195; 435/212; 435/219; 435/221; 435/222; 435/223; 435/229; 510/114; 510/392; 510/515
(58) Field of Search ............................... 435/4, 6, 69.1, 435/183, 195, 212–229; 510/114, 392, 515

(56) References Cited

U.S. PATENT DOCUMENTS

| 4,797,362 A | 1/1989 | Takeuchi et al. |
| 5,079,154 A | 1/1992 | Ito et al. |
| 5,344,770 A | 9/1994 | Hitomi et al. |
| 5,635,468 A | 6/1997 | Ara et al. |
| 6,376,227 B1 * | 4/2002 | Takaiwa et al. ............ 435/219 |

FOREIGN PATENT DOCUMENTS

| JP | 61-280278 | 12/1986 |
| JP | 4-197182 | 7/1992 |
| JP | 5-211868 | 8/1993 |
| JP | 6-70765 | 3/1994 |
| JP | 9-121855 | 5/1997 |
| JP | 9-121856 | 5/1997 |

* cited by examiner

Primary Examiner—Manjunath Rao
(74) Attorney, Agent, or Firm—Oblon, Spivak, McClelland, Maier & Neustadt, P.C.

(57) ABSTRACT

An alkaline protease having the following properties; a gene encoding the same; a microorganism producing the same; and washing compositions containing the same; (i) acting over a broad pH value range of 4 to 13 and achieving, at pH 6 to 12, 80% or more the activity at the optimum pH value; (ii) when treated at 40° C. for 30 minutes, being stable over a pH value range of 6 to 11; (iii) having an isoelectric point of about 8.9 to 9.1; and (iv) having casein digesting activity that is not inhibited by oleic acid. The alkaline protease of the present invention is highly stable to various surface active agents and fatty acids, and exhibits high stability to oxidizing agents, and is therefore useful as an enzyme to be used in detergents for automatic dishwashers and laundry detergents, both containing bleaching components.

14 Claims, 6 Drawing Sheets

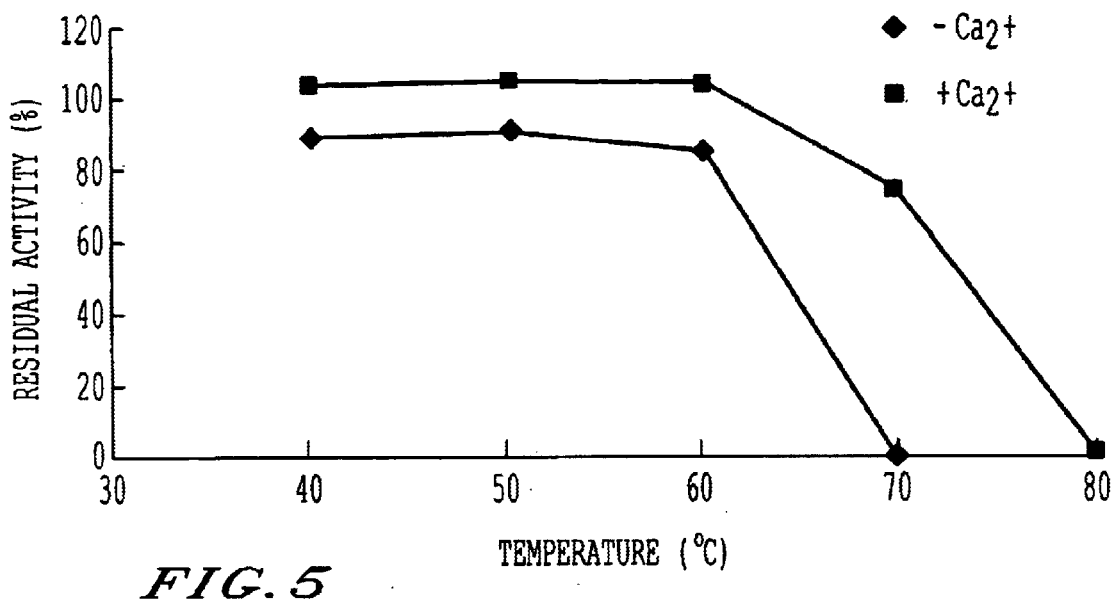
FIG. 5
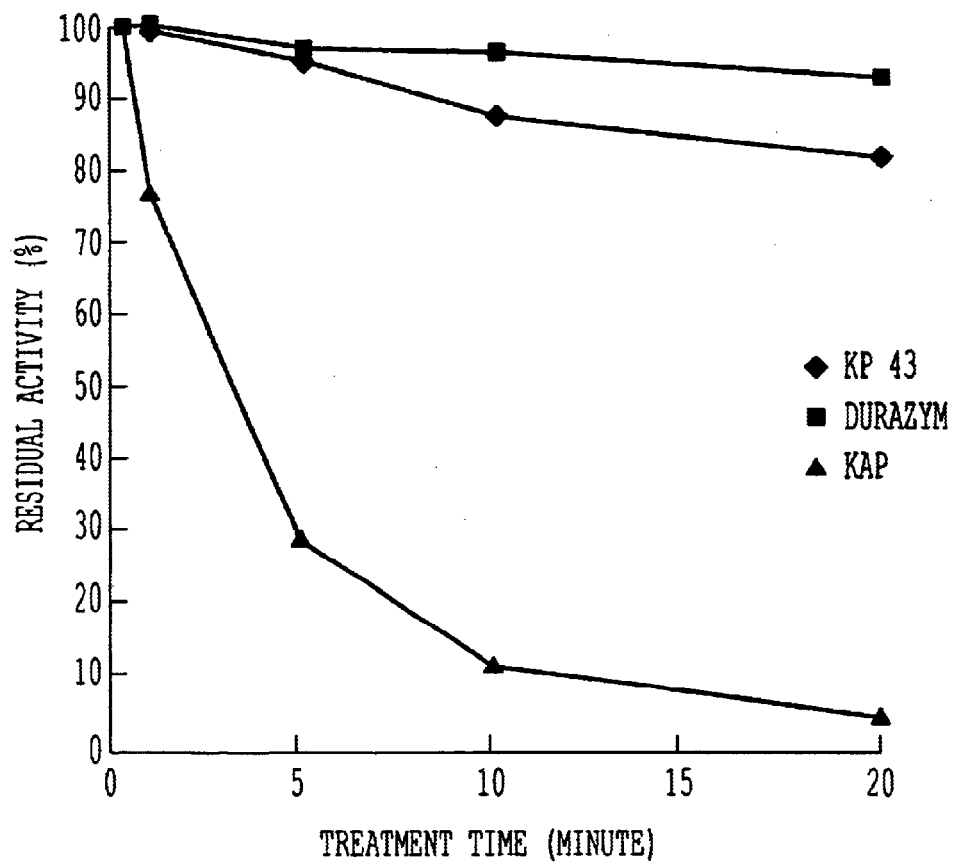
FIG. 6  STABILITY TO AN OXIDANT (50mM $H_2O_2$)

| | |
|---|---|
| N-terminal sequence of KP-9860 protease | NDVARHIVKADVAQSSYGLY |
| N-terminal sequence of 15kDa partially degraded product | GIVKADVAQSSYGL |
| N-terminal sequence of 18kDa partially degraded product | IKPDVMAPGTYIL |
| N-terminal sequence of 25kDa partially degraded product | NAITVGATENLRPSFGSYAD |
| N-terminal sequence of 28kDa partially degraded product | KNDMVILFAAGNEGPN |

*FIG. 7*

```
              I    V    K    A    D    V    A    Q
9860-N2    5'  ATT  GTT  AAA  GCT  GAT  GTT  GCT  CAA  3'
                C    C    G    C    C    G    C    G
                A    A         A    A         A    A
                                    G              G    G 9860-18k-RV 3' TAT  TTT  GGT  CTA  CAT  TACN CGT  GG   5'
                A    C    C    G    C              C
                G         A         A         A    A
                                    G         G         G

I    K    P    D    V    M    A    P
9860-18k   5'  ATT  AAA  CCT  GAT  GTT  ATG  GCT  CC   3'
                C    G    C    C    C         C
                A         A    A    A         A
                          G         G              G 9860-25k-RV 3' TTA  CGT  TAT  TGT  CAT  CCT  CGT  TGT  5'
                G    C    A    C    C    C    C    C
                     A    G    A    A    A    A    A
                     G         G    G    G    G    G

N    A    I    T    V    G    A    T    E    N
9860-25k   5'  ATT  ACT  GTT  GGT  GCT  ACT  GAA  AA   3'
                C    C    C    C    C    C    G
                A    A    A    A    A    A
                G    G    G    G    G 9860-28k-RV 3' TTA  CTA  TAC  CAT  TAT  AAT  AAA  CG   5'
                G    G         C    A    GC   G
                                    A    G    A
                                    G         G

N    D    M    V    I    L    F    A
9860-28k   5'  AAT  GAT  ATG  GTT  ATT  TTT  TTT  GC   3'
                C    C         C    C    C    C
                                    A    A    A
                                    G              G
```

FIG.8

ALKALINE PROTEASE

This application is a Continuation of U.S. application Ser. No. 09/509,814, filed on Apr. 6, 2000, now U.S. Pat. No. 6,376,227, Apr. 23, 2002, which is a 371 of PCT/3P98/04528, filed Oct. 7, 1997.

TECHNICAL FIELD

The present invention relates to an alkaline protease useful as an enzyme incorporated in a detergent; a gene encoding the same; a microorganism producing the same; and a detergent composition containing the same.

BACKGROUND ART

Protease has been widely used in a variety of detergents, such as laundry detergents; cosmetic compositions; bath additives; food-modifying agents; and pharmaceuticals such as digestive aids and antiphlogistics.

Of these, proteases used in detergents are produced in largest amounts on an industrial scale and thus account for a significant part of commercial supply. Examples of such proteases include Alcalase, Savinase (product of Novo Nordisk), Maxacal (product of Genencor), Blap (Product of Henkel), and Protease K (KAP, product of Kao Corporation).

Meanwhile, attempts have been made to improve the performance of enzymes used in detergents. For example, Japanese Patent Application Laid-Open (kokai) No. 6-70765 discloses an enzyme having high stability to heat and a surfactant. Japanese Patent Application Laid-Open (kokai) No. 9-121855 discloses an enzyme which acts on insoluble proteins such as keratin and has a high specific activity. Japanese Patent Application Laid-Open (kokai) Nos. 5-211868 and 9-121856 disclose an enzyme having excellent activity in a low temperature range. European Patent No. 0130756 discloses a method for enhancing stability of an enzyme to an oxidizing agent.

In many cases, soils on laundry comprise a plurality of components such as lipids and solid particles other than protein. Therefore, there is demand for a detergent having excellent detergency to such complex soils. In order to meet the demand, generally a plurality of enzymes and surfactants have been incorporated into a detergent.

However, even though a plurality of enzymes are incorporated, their effects cannot be fully exerted if, in the presence of complex soils, the enzymes are unstable and do not exhibit constant and sufficient activity. Conventional enzymes are unsatisfactory in this point.

DISCLOSURE OF THE INVENTION

In view of the foregoing, the present inventors have discovered an alkaline protease which has a constant casein-degrading activity even in the presence of a fatty acid at a high concentration and exhibits excellent detergency even under complex soil conditions; e.g., soils containing protein and sebum.

Accordingly, in one aspect of the present invention, there is provided an alkaline protease which has the following physicochemical properties:

(i) Acting pH range
acting over a wide pH range of 4–13 and exhibiting, at a pH of 6–12, 80% or more the activity at the optimum pH;

(ii) Stable pH range
being stable over a pH range of 6–11 when treated at 40° C. for 30 minutes;

(iii) Isoelectric point
having an isoelectric point of approximately 8.9–9.1; and (iv) Effect of a fatty acid
casein-degrading activity not being inhibited by oleic acid.

In another aspect of the present invention, there is provided a gene encoding the above-described alkaline protease.

In still another aspect of the present invention, there is provided a microorganism producing the above-described alkaline protease.

In yet another aspect of the present invention, there is provided a detergent composition containing the above-described alkaline protease.

BRIEF DESCRIPTION OF THE DRAWINGS

FIG. 5 shows the effects of temperature on the stability of alkaline protease KP43. FIG. 6 shows the effect of an oxidizing agent (50 mM hydrogen peroxide) on the activity of alkaline protease KP43. FIG. 7 shows N-terminal sequences of KP9860 protease and partially degraded products thereof SEQ ID NOS:9–13). FIG. 8 shows primer sequences (SEQ ID NOS: 14–20) designed from an N-terminal sequence of KP9860 protease (SEQ ID NOS: 9–13).

BEST MODE FOR CARRYING OUT THE INVENTION

Figure 1:
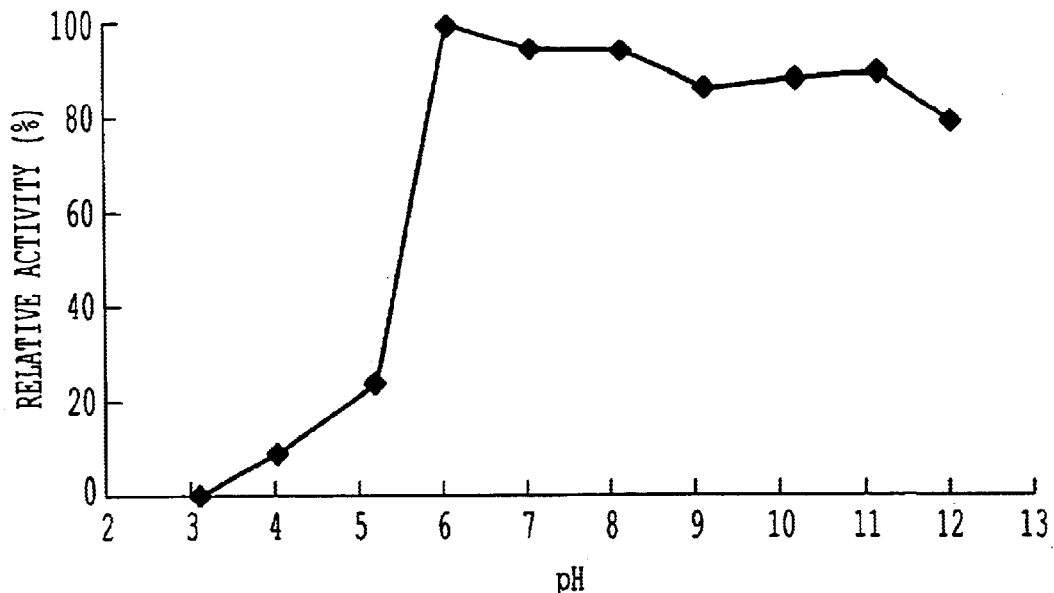
FIG. 1 shows the the effects of pH on the activity of alkaline protease KP43.

The alkaline protease of the present invention has the above-described physicochemical properties (i) through (iv). Of these, property (iv) is particularly important. The alkaline protease has a casein-degrading activity in the presence of 10 mM of oleic acid, a component of sebum, as high as that in the absence of oleic acid.

The alkaline protease of the present invention preferably has (v) an estimated molecular weight of approximately 43,000 as determined by SDS-polyacrylamide gel electrophoresis (SDS-PAGE).

Particularly preferred is an alkaline protease having, in addition to properties (i) through (v), properties (vi) through (ix) as described below.

(vi) Acting temperature and optimum temperature
acting at an optimum temperature of 60° C.–70° C., and also acting at a temperature as low as 20° C. or lower;
(vii) Effects of metal ions
activity being inhibited by $Hg^{2+}$ and $Cu^{2+}$ and thermal stability being enhanced by $Ca^{2+}$;
(viii) Effects of inhibitors
activity not being inhibited by ethylenediaminetetraacetic acid (EDTA) and p-chloromercurybenzoic acid (PCMB) and activity being inhibited by diisoproyl fluorophosphate (DFP) and phenylmethanesulfonyl fluoride (PMSF); and (ix) Effects of surface active agents
activity not being inhibited by linear sodium alkylbenzenesulfonate, sodium polyoxyethylene alkyl sulfate, sodium dodecyl sulfate, sodium α-olefinsulfonate, or α-sulfofatty acid ester.

The alkaline protease of the present invention preferably has an amino acid sequence shown in SEQ ID NOS: 1 or 2, or such a sequence in which one or more amino acids are deleted, substituted, or added. SEQ ID NO: 1 differs from SEQ ID NO: 2 in that lysine at the 3$^{rd}$ position in SEQ ID NO: 2 is deleted. Xaa in SEQ ID NOS: 1 and 2 refers to an arbitrary amino acid. Preferable amino acids for Xaa at each position in SEQ ID NO: 2 are shown in the following Table.

TABLE

| position | | Position | |
|---|---|---|---|
| 24 | Ser or Asn | 30 | Gly or Asp |
| 33 | Asn or Thr | 47 | Ala or Val |
| 48 | Lys or Ser | 54 | Gly or Arg |
| 71 | Pro or Leu | 75 | Gln or Leu |
| 90 | Ile or Val | 103 | Gln or Lys |
| 106 | Lys or Thr | 129 | Lys or Gln |
| 131 | Ala or Lys | 132 | Thr or Val |
| 133 | Ser or Arg | 134 | Thr or Ser |
| 147 | Ile or Lys | 149 | Arg or Lys |
| 161 | Glu or Thr | 166 | Val or Leu |
| 173 | Lys or Asn | 184 | Gln or Glu |
| 188 | Phe or Tyr | 189 | Ala or Val |
| 190 | Ile or Ala | 195 | Leu or His |
| 287 | Ser or Ala | 307 | Gly or Ser |
| 325 | Tyr or Phe | 370 | Gly or Arg |
| 432 | Phe or Tyr | 502 | Ile or Val |
| 532 | Ser or Ala | 542 | Ser or Thr |
| 585 | Gln or Arg | 592 | Thr or Ser |
| 593 | Ser or Ala | 595 | Tyr or Phe |
| 596 | Asn or Asp | 597 | Asp or Asn |
| 612 | Ala or Ser | 633 | Thr or Asn |

Deletions, substitutions, and additions in the alkaline protease of the present invention are not particularly limited. However, the amino acid sequence shown in Sequence No. 1 or 2 is preferably conserved in the amount of 70% or more, more preferably 80% or more, particularly preferably 90% or more.

Examples of the alkaline protease include alkaline proteases having an amino acid sequence shown by SEQ ID NOS: 4, 6, or 8, or such a sequence in which one or more amino acids are deleted, substituted, or added.

The alkaline protease of the present invention may be produced by cultivating alkaline protease-producing microorganisms belonging to the genus Bacillus and collecting the enzyme from the culture broth. Examples of alkaline protease-producing microorganisms according to the present invention include wild strains belonging to the genus Bacillus and a transformant containing a gene encoding a peptide having the above-described amino acid sequence. Examples of the wild strains include KP-43, KP-1790, and KP-9860. Mycological characteristics of these strains are shown below.

TABLE 1-a

| | KP43 | KP1790 | KP9860 |
|---|---|---|---|
| A. Morphological characteristics | | | |
| (a) Gram's staining | positive | positive | positive |
| (b) Aminopeptidase | undefined | undefined | undefined |
| (c) Movement | yes | yes | yes |

TABLE 1-a-continued

| | KP43 | KP1790 | KP9860 |
|---|---|---|---|
| (d) Flagella | peritrichous flagella | peritrichous flagella | peritrichous flagella |
| (e) Spores (type, shape, site, swell) | sporogenous, eliptical, central, none | sporogenous, eliptical, central, none | sporogenous, eliptical, central to terminal, swollen |
| B. Physiological characteristics | | | |
| (a) Nitrate reduction | negative | negative | negative |
| (b) Production of indole | negative | negative | negative |
| (c) Growth pH range | can grow at pH 6.2–11.7, well grow at pH 8–10 | can grow at pH 6.2–11.7, well grow at pH 8.5–10 | can grow at pH 6.2–10.0, well grow at pH about 9 |
| (d) Resistance to sodium chloride | cannot grow under ≧ 7% NaCl | cannot grow under ≧ 7% NaCl | cannot grow under ≧ 7% NaCl |
| (e) Growth temperature range | 10–40° C. | 10–40° C. | 20–40° C. |
| (f) β-Galactosidase | positive | positive | positive |
| (g) Arginine dihydrolase | negative | negative | negative |
| (h) Lysine dihydrolase | negative | negative | negative |
| (i) Oxydase | positive | positive | positive |
| (j) Utilization of citric acid | negative | negative | negative |
| (k) Utilization of urea | negative | negative | negative |
| (l) Catalase | positive | positive | positive |
| (m) Gas production from glucose and nitrate | negative | negative | negative |
| (n) Growth under anaerobic conditions | negative | negative | negative |
| (o) V-P test | negative | negative | negative |

TABLE 1-b

| | KP43 | KP1790 | KP9860 |
|---|---|---|---|
| (p) Acid production from sugar | | | |
| D-Glucose | + | ± | + |
| L-Arabinose | – | – | – |
| D-Xylose | – | – | – |
| D-Mannitol | + | + | + |
| D-Galactose | ± | – | – |
| Sucrose | + | + | + |
| D-Mannose | + | ± | + |
| Inositol | – | – | – |
| D-Sorbitol | + | – | – |
| Trehalose | ± | + | + |
| Lactose | – | – | – |
| Glycerol | – | – | – |
| Maltose | + | ± | + |
| D-Fructose | + | + | + |
| Raffinose | – | – | – |
| Melibiose | + | – | – |
| Starch | + | + | + |

Based on the above-described mycological characteristics, the three strains were examined by reference to the pertinent descriptions in "Bergey's Manual of Systematic Bacteriology" (Williams & Wilkins Co., 1984), and were considered to belong to the genus Bacillus. However, these strains are novel microorganisms in that characteristics of these species do not completely match those of known species belonging to the genus Bacillus. Thus, the three strains were deposited with National Institute of Bioscience and Human Technology, Agency of Industrial Science and Technology (1–3, Higashi 1-chome, Tsukuba-shi, Ibaraki, 305–0046, JAPAN) as Bacillus sp. KSM-KP43 (FERM BP-6532), Bacillus sp. KSM-KP1790 (FERM BP-6533), and Bacillus sp. KSM-K9860 (FERM BP-6534) (Date of original deposit: Sep. 18, 1996).

In order to produce the alkaline protease of the present invention by use of the above-described strains, the strains are inoculated in a medium containing an assimilablecarbon source, a nitrogen source, and essential nutrients and are cultured through a customary method.

Collection and purification of a target alkaline protease from the thus-obtained culture broth can be performed according to conventional methods applicable to the collection and purification of common enzymes. For example, cells are separated from the culture broth by centrifugation or filtration, and the target alkaline protease can be obtained from the supernatant through a customary purification method. The thus-obtained enzyme liquid may be used as such or may be further purified and crystallized through a known method.

Alternatively, the alkaline protease of the present invention may be produced through the following steps: obtaining a gene encoding the alkaline protease; preparing a recombinant vector by use of the gene; transforming a host cell by use of the recombinant vector; cultivating the obtained transformant; and collecting the target alkaline protease from the cultured product.

The gene encoding the alkaline protease of the present invention may be cloned from any of the three above-described strains. Cloning may be performed through known methods. Examples of the methods include (1) the shot gun method comprising preparation of a DNA fragment through complete or partial digestion of chromosomal DNA by use of an appropriate restriction endonuclease; combination of the fragment into a suitable vector; and expression through introduction to *Escherichia coli* or *Bacillus subtilis*, and (2) a method comprising synthesis of an appropriate primer and cloning a target gene through PCR.

Examples of the nucleotide sequence of the alkaline protease of the present invention are shown in SEQ ID NOS: 3, 5 and 7. The nucleotide sequence is not limited to SEQ ID NOS: 3, 5 or 7, and acceptable sequences may include a nucleotide sequence encoding the amino acid sequence shown in SEQ ID NOS: 1 or 2, and a nucleotide sequence encoding such an amino acid sequence in which one or more amino acids are deleted, substituted, or added. Of these, nucleotide sequences represented by SEQ ID NOS: 3, 5 and 7, or such sequences in which one or more amino acids are deleted, substituted, or added are preferred. In these cases, deletion, substitution, or addition preferably occurs within the above-described variation of amino acid sequence.

In order to prepare a recombinant vector including the above-described gene encoding an alkaline protease, the gene may be incorporated into an arbitrary vector suitable for expression of the gene in a host of interest. Examples of the vectors include pUC18, pBR322, and pUC19 in the case in which *Escherichia coli* serves as a host and pUB110 in the case in which *Bacillus subtilis* serves as a host.

A host is transformed by use of the thus-obtained recombinant vector through a customary method such as the protoplast method or the competent cell method. Although no particular limitation is imposed on the host, microorganisms are preferred. Examples include Gram-positive bacteria such as microorganisms belonging to the genus Bacillus, Gram-negative bacteria such as *Escherichia coil*, yeast belonging to Saccharomyces, and fungus belonging to Aspergillus.

In order to produce the alkaline protease of the present invention through culturing of the obtained transformant, cultivation, collection, and purification may be performed in accordance with a procedure employed in the case in which the above-described wild strain is used.

As described above, the alkaline protease of the present invention has excellent resistance to alkaline conditions and excellent protease activity even in the presence of lipids. Thus, the alkaline protease is useful for an enzyme incorporated in a variety of detergent compositions.

No particular limitation is imposed on the amount of the above-described alkaline protease incorporated into a detergent composition, and the amount is preferably 0.1–5000 U based on 1 kg, particularly preferably 1–500 U, of the detergent composition.

Known detergent components may be incorporated into the detergent composition of the present invention containing the alkaline protease. For example, components described in WO94/26881 (p. 5, upper-right column, line 14—lower-right column, line 29) may be employed.

A surfactant is incorporated into the detergent composition in an amount of 0.5–60 wt. % (hereinafter simply referred to as "%"), particularly preferably 10–45%, into a powdery detergent composition and in an amount of 20–50% into a liquid detergent composition. When the detergent composition of the present invention serves as a bleaching detergent composition or a detergent composition for an automated dishwasher, a surfactant is typically incorporated in an amount of 1–10%, preferably 1–5%.

A divalent metal ion scavenger is incorporated in an amount of 0.01–50%, preferably 5–40%.

An alkali agent and an inorganic salt are incorporated in an amount of 0.01–80%, preferably 1–40%.

An anti-redeposition agent is incorporated in an amount of 0.001–10%, preferably 1–5%.

The detergent composition may contain an enzyme other than the alkaline protease of the present invention. Examples include cellulose, amylase, protopectinase, pectinase, lipase, hemicellulase, β-glucosidase, glucose-oxidase, and cholesterol-oxidase. These enzymes are incorporated in an amount of 0.001–5%, preferably 0.1–3%.

A bleaching agent such as hydrogen peroxide or percarbonate is preferably incorporated in an amount of 1–10%. When a bleaching agent is incorporated, a bleach-activator may be incorporated in an amount of 0.01–10%.

Examples of fluorescent agents incorporated into the composition include a biphenyl compound, such as Cinopearl CBS-X, and a stilbene compound such as DM-type fluorescent agent. The fluorescent agent is preferably incorporated in an amount of 0.001–2%.

The above-described detergent composition may be processed into a variety of forms such as liquid, powder, and granules. The detergent composition may be used for laundry, an automated dishwasher, drain pipes, and dentures, and may be used as a bleaching agent.

EXAMPLES

Example 1

Screening for Alkaline Protease-producing Microorganisms

A soil sample (1 g) was suspended in physiological saline (10 ml) and thermally treated at 80° C. for 10 minutes, followed by inoculation in liquid enrichment medium for protease-producing microorganisms, the medium having the following composition, to thereby culture at 20° C. After subculture enrichment was repeated about three times in the same medium, the cultivated product was smeared onto a plate for judging protease-production and cultivated at 20° C. for 5–7 days. Colonies around which a transparent zone was formed by dissociation of skim milk were selected for collection of protease-producing microorganisms. By means of the above procedure, the Bacillus sp KSM-KP43 strain, the KSM-KP1790 strain, and the KSM-KP9860 strain were obtained as alkaline protease-producing microorganisms.

TABLE 2

| Composition of liquid enrichment medium for screening (pH 11) | |
|---|---|
| Monopotassium phosphate | 0.1% |
| Magnesium sulfate | 0.02% |
| Yeast extract (Difco) | 0.05% |
| Keratin (Tokyo Kasei) | 1.0% |
| Glucose | 0.5% |
| Sodium carbonate | 0.3% |
| Agar plate medium for screening | |
| Nutrient agar (Difco) | 2.3% |
| Skim milk (Difco) | 0.3% |
| Sodium carbonate | 1.0% |

Example 2

The Bacillus sp KSM-KP43 strain obtained in Example 1 was inoculated in a liquid medium comprising polypeptone S (1%), yeast extract (0.05%), potassium phosphate (0.1%), magnesium sulfate (0.02%), glucose (separately sterilized) (1%), and sodium carbonate (separately sterilized) (0.5%) to thereby be cultivated at 30° C. for 24 hours. The concentration of enzyme in the supernatant liquid was about 1.5 U/L. The supernatant liquid which had been centrifugally separated from cells at 4° C. was added with pulverized ammonium sulfate under stirring so as to attain 90% of saturated concentration. The solution was maintained under stirring at 4° C. for an entire day and night and the resultant precipitate was centrifugally collected. The obtained precipitate was dissolved in 10 mM of a Tris-hydrochloric acid buffer solution (pH 7.5) containing 5 mM of calcium chloride, followed by dialysis through the buffer solution. Subsequently, the dialyzed liquid was applied to a DEAE-Sepharose FF column (product of Pharmacia) which had been equilibrated with 10 mM of a Tris-hydrochloric acid buffer solution (pH 7.5) containing 5 mM of calcium chloride, to thereby collect the non-absorbed fraction. The fractionated liquid was dialyzed through 50 mM of HEPES buffer solution (pH 7.5) containing 2 mM of calcium chloride and was applied to a SP-Sepharose FF column which had been equilibrated with the same buffer solution, to thereby collect an active fraction which has eluted slightly after the non-absorbed fraction. While the active fraction, which had a recovery ratio of 15%, was used as a sample, SDS-polyacrylamide electrophresis was carried out, and as a result, a single band was obtained for the respective enzyme.

Example 3

The obtained Bacillus sp KSM-KP1790 strain and KSM-KP9860 strain were cultivated in the same medium as in Example 2 and the alkaline protease was purified in the same manner as in Example 2.

Example 4

Enzymatic properties of the alkaline proteases obtained in Example 2 and 3 were examined. The methods and results of the experiments are described below.
I. Materials and Methods for Experiments
(1) Methods for Activity Measurement
(a) Method in Which Casein is Used as a Substrate After 1 mL of 50 mmol/L of various buffer solutions containing 1% (w/v) Casein (Hammerstein: product of Merck Inc.) was maintained at 40° C. for 5 minutes, 0.1 mL of an enzyme solution was added to the solution, followed by incubation at 40° C. for 10 minutes. 2 mL of a TCA solution (0.11 mol/L trichloroacetic acid: 0.22 mol/L sodium acetate: 0.33 mol/L acetic acid) was added to stop the reaction and the mixture was left to stand at room temperature for 10 minutes. Subsequently, acid-denatured protein was filtered (No. 2 filter paper: product of Whattmann). To 0.5 mL of the filtrate, 2.5 mL of alkaline copper reagent (1% (w/v) sodium potassium tartrate: 1% (w/v) copper sulfate: 2% (w/v) sodium carbonate, 0.1 mol/L sodium hydroxide= 1:1:100 (v/v)) was added, and after the solution was maintained at 30° C. for 10 minutes, 0.25 mL of diluted phenol reagent (phenol reagent (product of Kanto Chemical) diluted two-fold with deionized water) was added, and after being maintained at 30° C. for 30 minutes, the solution was subjected to an absorbance measurement at 660 nm. The following solution was used as a blank: to the above-described system of enzyme reaction, a reaction termination solution was mixed and then the enzyme solution was added.

One unit (P.U) of enzymatic activity was defined as the amount of enzyme that released acid-soluble protein degradation products equivalent to 1 mmol of tyrosine per minute under the above reaction conditions.
(b) Method in Which Synthetic Oligo-peptide is Used as a Substrate 0.05 mL of 50 mmol/L synthetic oligo-peptide solution (succinyl-alanyl-alanyl-prolyl-leucine para-nitroanilide dissolved in dimethyl sulfoxide) was mixed into 0.9 mL of 100 mmol/L boric acid buffer solution (pH 10.0, containing 2 mmol/L of calcium chloride), and after the solution was maintained at 30° C. for 5 minutes, 0.05 mL of an enzyme solution was added, followed by incubation at 30° C. for 10 minutes. 2 ml of 5% (w/v) citric acid was added to stop the reaction and absorbance at 420 nm was measured.

One unit (U) of enzymatic activity was defined as the amount of enzyme that released acid-soluble protein degradation products equivalent to 1 mmol of tyrosine per minute under the above reaction conditions.
(c) Method in Which Hemoglobin is Used as a Substrate According to the method by Anson (M. L. Anson, J. Gen. Physiol. 22, 79(1983)), hemoglobin of bovine blood serum was denatured by use of urea and adjusted to pH 10.5 with sodium hydroxide. 0.1 mL of an enzyme solution $(1.0 \times 10^{-5} - 1.0 \times 10^{-3}$ A.U) was added to 0.5 mL of the substrate solution (2.2% in terms of hemoglobin), and the resultant solution was incubated at 25° C. for 10 minutes. To the resultant solution, 1.0 mL of 4.9% tirchloroacetic acid was added to stop the reaction. After completion of the reaction, centrifugation (3,000 rpm, 10 minutes) was carried out and protein degradation products in the supernatant liquid were quantitatively determined according to the Folin-Lowry method (O. H. Lowry et al., J. Biol. Chem., 193, 265(1951)).

One unit (A. U) of enzymatic activity was defined as the amount of enzyme that released acid-soluble protein degradation products equivalent to 1 mmol of tyrosine per minute under the above reaction conditions.
(2) Optimum pH 0.1 mL of an enzyme solution $(3.0 \times 10^{-5}$ mP. U) was added to 1 mL of 50 mmol/L Britton-Robinson buffer solution containing 1% (w/v) casein, and activity was measured according to the casein method.
(3) pH Stability An enzyme solution $(8.0 \times 10^{-4}$ mP. U.) was mixed into Britton-Robinson buffer solution (20 mmol/L, containing 2 mmol/L calcium chloride), followed by treatment at 40° C. for 30 minutes or at 10° C. for 24 hours. After ice-cooling, the treated solution was diluted 40-fold with 50 mmol/L boric acid buffer solution, followed by measurement of residual activity according to the method in which casein is used as a substrate.

(4) Optimum Temperature 0.1 mL of the enzyme solution ($2.0 \times 10^{-5}$ mP. U.) was added to 1 mL of 50 mmol/L boric acid buffer solution (pH 10.0) containing 1% (w/v) casein, and activity of the enzyme was measured at temperatures between 10–80° C. according to the casein method.

The activity measurements were conducted in both systems; i.e., in the presence of and in the absence of 5 mmol/L calcium chloride.

(5) Heat Stability

An enzyme solution ($2.5 \times 10^{-4}$ mP. U.) was added to 20 mmol/L boric acid buffer solution (pH 10.0) in both systems; i.e.,. in the presence of and in the absence of 5 mmol/L calcium chloride, and thermally treated at the appropriate temperature for 10 minutes. After being cooled with ice, the treated solution was diluted 5-fold with 50 mmol/L boric acid buffer solution (pH 10.0), and residual activity was measured using casein as a substrate.

(6) Effects of Metal Ions

An enzyme solution ($4.0 \times 10^{-4}$ mP. U.) was added to 20 mmol/L boric acid buffer solution (pH 10.0) containing 1 mmol/L various metal salts, and the resultant solution was incubated at 30° C. for 20 minutes. The solution was diluted 5-fold with 50 mmol/L boric acid buffer solution (pH 10.0), followed by measurement of activity using casein as a substrate.

(7) Effects of Inhibitors

The enzyme solution ($1.0 \times 10^{-3}$ mP. U.) was added to 10 mmol/L phosphoric acid buffer solution (pH 7.0) containing various inhibitors so as to attain a predetermined concentration, and the solution was incubated at 30° C. for 20 minutes. Subsequently, the solution was diluted 20-fold with deionized water, and residual activity was measured using casein as a substrate.

(8) Effects of Surfactants

An enzyme solution ($7.0 \times 10^{-4}$ mP. U.) was added to 100 mmol/L boric acid buffer solution containing dissolved surfactants in an amount of 1%, and the resultant solution was incubated at 40° C. for 4 hours. The solution was diluted 20-fold with 50 mmol/L boric acid buffer solution (pH 10.0), and residual activity was measured using casein as a substrate.

(9) Effects of Oxidizing Agent (Hydrogen Peroxide)

2.7 mL of Britton-Robinson buffer solution containing hydrogen peroxide and calcium chloride (final concentration: 50 mmol/L hydrogen peroxide, 2 mmol/L calcium chloride, 20 mmol/L Britton-Robinson) (pH 8.0) was maintained at 30° C. for 15 minutes, and then 0.3 mL of an enzyme solution was added. With the passage of time, 0.8 mL of the resultant solution was sampled in a previously prepared test tube containing 5 μL of catalase (Boehringer Mannheim Co.: 20 mg/L), to thereby stop the oxidation reaction. Each sample was suitably diluted with 2 mmol/L calcium chloride, and residual activity was measured according to the method in which synthetic oligo-peptide is used as a substrate.

(10) Effects of Fatty Acids

By use of 50 mM phosphoric acid buffer solution (pH 7) containing 1% (w/v) casein as a substrate solution, a reaction was carried out in the presence of 0–10 mM sodium oleate at 20° C. for 15 minutes, and activity was measured using casein as a substrate.

II. Results (1) Optimum pH

Effects of pH on three kinds of protease (KP43, KP1790, and KP9860) were examined. FIG. 1 shows the activities of KP43 at each pH value normalized with respect to activity at optimum pH (100%), indicating that the optimum working pH range of the proteases of the present invention is 6–12. Thus, these enzymes exhibit a high protein-degradation activity in the extensively broad working pH range.

(2) pH Stability

Figure 2:
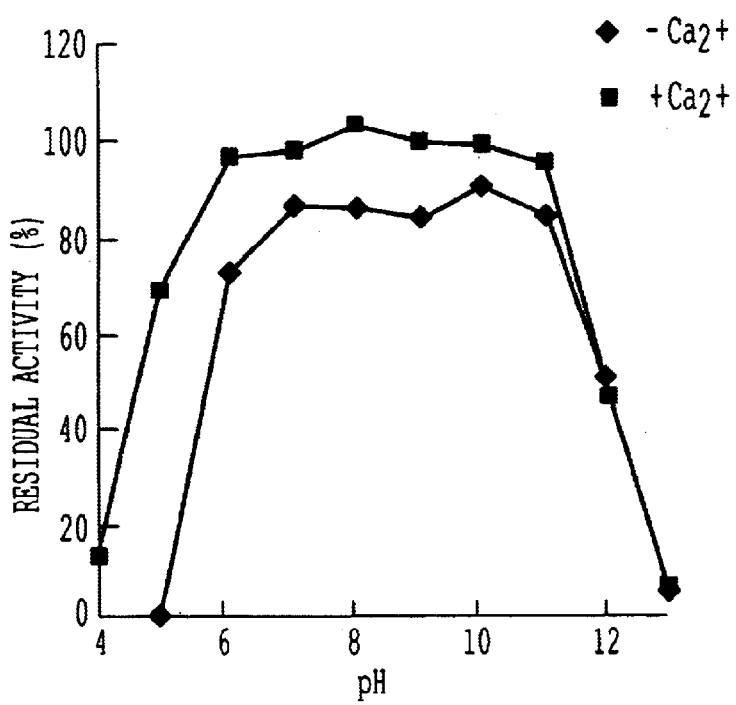
FIG. 2 shows the effects of pH on the stability of alkaline protease KP43 (40° C., 30 minutes).
Figure 3:
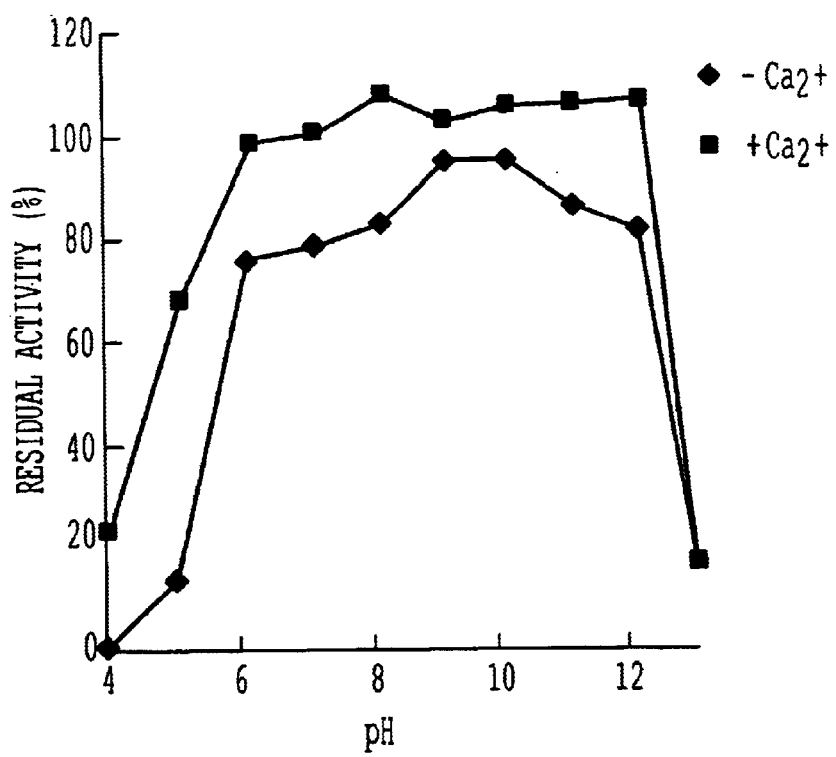
FIG. 3 shows the effects of pH on the stability of alkaline protease KP43 (10° C., 24 hours).

After being allowed to stand at 40° C. for 30 minutes or at 10° C. for 24 hours, the residual activity of KP43 was measured over a range of pH values. FIGS. 2 and 3 show the residual activities normalized with respect to the enzyme activity before treatment (100%). The results show that the enzymes of the present invention are stable over the pH range of 6–12 after treatment at 40° C. for 30 minutes, and that addition of calcium ions improves enzyme stability at pH 5. Similarly, the results show the enzymes of the present invention are stable over the broad pH range of 5–12 after treatment at 10° C. for 24 hours.

(3) Optimum Temperature

Figure 4:
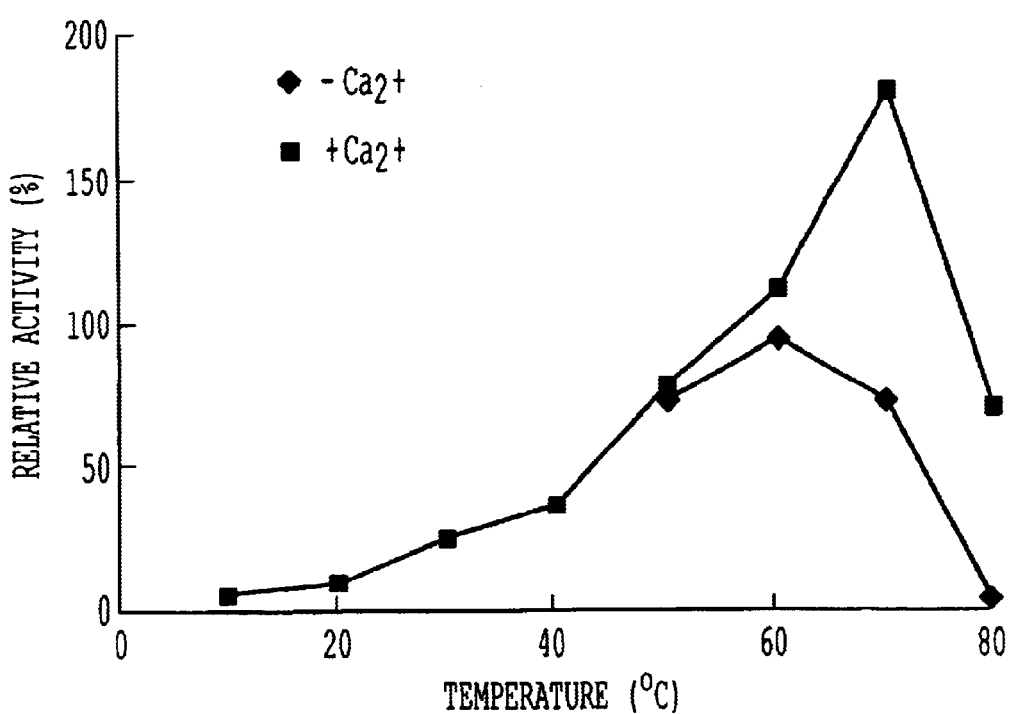
FIG. 4 shows the effects of temperature on the activity of alkaline protease KP43.

By use of casein as a substrate, the effects of temperature on the proteases were examined. FIG. 4 shows the activities of KP43 over a range of temperatures, normalized with respect to the highest activity in the absence of calcium ions (100%). The results indicate that in the absence of calcium ions the optimum temperature is 60° C., and in the presence of calcium ions the optimum temperature is 70° C. for all three kinds of proteases. Therefore, the results show that the optimum temperature is shifted upward by addition of calcium ions, as is the case with conventional proteases for a detergent.

(4) Heat Stability

Heat treatment was carried out for 10 minutes at temperatures in the range of 30–80° C. (pH 10.0, in the presence of and in the absence of 5 mmol/L calcium chloride), and residual activity was measured. FIG. 5 shows residual activity of KP43 at each treatment temperature, normalized with respect to the activity before treatment (100%). The results indicate that the proteases are stable at the temperature up to 60° C. in the absence of calcium chloride, and that addition of calcium chloride (5 mmol/L) has the effect of shifting temperature stability upward about 10° C. In comparison with commercially available detergent enzymes, these enzymes have high temperature stability; namely, stability comparable to that of Esperase, which exhibits the most excellent temperature stability among commercially available enzymes.

(5) Effects of Metal Ions

In 20 mmol/L boric acid buffer solution (pH 10), 3 kinds of proteases were treated with various metal salts (1 mmol/L) at 30° C. for 20 minutes and the residual activity was measured. Residual activity is normalized with respect to enzyme activity obtained for protease treated in the same manner except without the addition of metal salts (100%) (see Table 3.) The results show that the activity is inhibited by mercury chloride and silver nitrate but that the activity is extremely stable for other metal salts.

TABLE 3

| Metal salt | Residual activity (%) | | |
|---|---|---|---|
| (1 mM) | KP43 | KP1790 | KP9860 |
| not added | 100 | 100 | 100 |
| $AgNO_3$ | 66 | 70 | 45 |
| $NiCl_2$ | 92 | 95 | 96 |

TABLE 3-continued

| Metal salt | Residual activity (%) | | |
|---|---|---|---|
| (1 mM) | KP43 | KP1790 | KP9860 |
| $CaCl_2$ | 97 | 95 | 101 |
| $CoCl_2$ | 91 | 101 | 98 |
| $FeCl_3$ | 93 | 113 | 96 |
| $ZnCl_2$ | 85 | 94 | 91 |
| $CuCl_2$ | 91 | 96 | 94 |
| $HgCl_2$ | 38 | 37 | 33 |
| $MgCl_2$ | 92 | 103 | 100 |

Treatment conditions: 1 mM metal salt, 20 mM borate buffer (pH 10.0) 30° C., 20 minutes (6) Effects of Various Inhibitors Effects of general enzyme inhibitors on the alkaline proteases of the present invention were examined. A variety of inhibitors were added to 10 mmol/L phosphoric acid buffer solution (pH 7.0) so as to attain the predetermined concentration, and the resultant solution was incubated at 30° C. for 20 minutes, after which residual activity was measured. The residual activity is normalized with respect to the enzyme activity obtained for protease treated in the same manner as described above in the absence of inhibitors (100%) (refer to Table 4). The results indicate that for all three kinds of proteases activity was inhibited by diisopropyl fluorophosphoric acid (DFP), phenylmethanesulfonyl fluoride (PMSF), and chymostatin, which are known inhibitors of serine protease. Therefore, the proteases of the present invention are considered to have serine residue in its active center. In contrast, effects of actinomycetes-derived antipine and leupeptin, which has been reported to inhibit serine protease, were not found.

TABLE 4

| | | Residual activity (%) | | |
|---|---|---|---|---|
| Inhibitor | Concentration(mM) | KP43 | KP1790 | KP9860 |
| free | — | 100 | 100 | 100 |
| EDTA | 5 | 110 | 97 | 101 |
| EGTA | 5 | 92 | 91 | 90 |
| o-Phenanthroline | 5 | 100 | 103 | 100 |
| DTT | 5 | 104 | 102 | 105 |
| PCMB | 1 | 125 | 115 | 126 |
| NEM | 5 | 97 | 100 | 100 |
| DFP | 1 | 14 | 17 | 16 |
| PMSF | 1 | 0 | 0 | 0 |
| Chymostatin | 0.1 | 87 | 87 | 80 |
| Antipine | 0.1 | 103 | 99 | 97 |
| Leupeptin | 0.1 | 102 | 101 | 93 |
| E-64 | 0.1 | 104 | 99 | 103 |
| Elastatinal | 0.1 | 99 | 102 | 102 |

EDTA ethylenediaminetetraacetic acid (Sigma)
EGTA ethyleneglycoltetraacetic acid (Sigma)
DTT dithiothreitol (Sigma)
PCMB p-chloromercury benzoate (Sigma)
NEM N-ethylmaleimide (Sigma)
DFP diisopropylfluorophosphoric acid (Sigma)
PMSF phenylmethanesulfonyl fluoride (Sigma)

(7) Effects of Surface Active Agents

Each protease was treated with a variety of 1% surface active agent at 40° C. for 4 hours in 0.1 mol/L Tris-hydrochloride buffer solution (pH 9.0), and residual activity was measured. Residual activity is normalized with respect to the enzyme activity in the case of no treatment (100%) (refer to Table 5.), indicating that the three kinds of enzymes are extremely stable to surfactants typified by linear alkylbenzenesulfonic acid (LAS). Accordingly, the enzymes are considered to be useful as a detergent component containing surfactants.

TABLE 5

| Surfactant | Residual activity | | |
|---|---|---|---|
| (concentration: 1%) | KP43 | KP1790 | KP9860 |
| free | 100 | 100 | 100 |
| Na linear alkylbenzenesulfonate (LAS) | 100 | 88 | 100 |
| Na polyoxyethylene alkylsulfate (ES) | 101 | 102 | 104 |
| Na dodecyl sulfate (SDS) | 104 | 97 | 103 |
| Na α-olefinsulfonate (AOS) | 100 | 111 | 100 |
| Na alkyl sulfate (AS) | 113 | 107 | 107 |
| α-Sulfofatty acid ester (α-SFE) | 112 | 113 | 105 |
| Softanol 70H | 109 | 109 | 104 |

Treatment conditions: 1% surfactant, 100 mM borate buffer (pH 10.0) 40° C., 4 hours (8) Effects of Oxidizing Agents Each protease was treated at 30° C. in 50 mmol/L Britton-Robinson buffer solution containing hydrogen peroxide (pH 8.0), and the residual activity was measured with passage of time. As shown in FIG. 6, KP43 exhibited much greater stability than that of commercially available Savinase or KAP and showed stability as high as that of Durazyme (Novo Nordisk), which was developed by imparting oxidizing agents-resistance to Savinase by use of protein engineering techniques.

(9) Effects of Fatty Acids

As shown in Table 6, the activity of alkaline proteases of the present invention was not inhibited by oleic acid, one of the components of sebum.

TABLE 6

| | Relative activity (%) in the presence of fatty acid | | | | |
|---|---|---|---|---|---|
| | oleic acid concentration (mM) | | | | |
| | 0 | 1 | 2 | 5 | 10 |
| KP43 protease | 100 | 100 | 100 | 103 | 119 |
| KP1790 protease | 100 | 100 | 100 | 103 | 121 |
| KP9860 protease | 100 | 100 | 100 | 100 | 106 |

Example 5

Cloning of a Gene Encoding KP9860 Protease (1) Preparation of Genomic DNA of KSM-KP9860

The KSM-KP9860 strain was cultivated in a liquid medium (0.5% glucose, 0.2% Polypepton-S, 0.05% yeast extract, 0.1% $KH_2PO_4.7H_2O$, 0.26% $NaCO_3$: pH 9.0) (500 mL) at 30° C. for two days, and the cells were collected by centrifugation. Genomic DNA was prepared from the obtained cells by the method of Saito and Miura (*Biochim. Biophys. Act*, 72, 619(1963)).

(2) Limited Proteolysis of KP9860 Protease

| 1) Denaturation of KP9860 protease | |
|---|---|
| KP9860 protease (5 mg/mL) | 45 μL |
| PMSF (100 mM) | 20 μL |
| EDTA (200 mN) | 10 μL |
| SDS (0.08 mg/mL) | 25 μL |

A protease solution with the above composition was heated in boiling water for 10 minutes. The protease solution was dialyzed against ammonium acetate (2 mM), to thereby remove SDS, EDTA, and PMSF, and was then lyophilized. Subsequently, the lyophilized protease was dissolved in distilled water (100 μL), to thereby serve as a sample of denatured protein.

| 2) Limited proteolysis by trypsin | |
| --- | --- |
| Denatured protein sample | 100 μL |
| Trypsin (1 μg/mL, Sigma) | 100 μL |
| 1M Tris-HCl (pH 7.5) | 50 μL |
| Distilled water | 750 μL |

Trypsin was allowed to react against the deratured protein prepared in 1) in an ice bath for 3 hours in the solution with the above composition. After addition of 300 μL of SDS (0.08 mg/mL), 100 μL of EDTA (200 mM) and 200 μL of PMSF (100 mM), limited proteolysis was terminated by heating in boiling water for 3 minutes.

SDS, EDTA, and PMSF were removed through dialysis against ammonium acetate (2 mM), and the solution was lyophilized. Subsequently, the lyophilized was dissolved in distilled water (100 μL), to thereby serve as a sample for SDS-PAGE.

3) Recovering of the Partially Degraded Product

The sample obtained in 2) was subjected to SDS-PAGE with 12% Ready-gel-J (product of Bio-Rad). Protein bands were detected through staining with quick CBB staining solution (product of Bio-Rad). The gel containing the protein band was cut with a razor, and the gel slice was crushed into pieces in a 1.5-mL tube. The buffer for SDS-PAGE (composition: glycine 14.4% (W/V), Tris 3.03%, SDS (product of Bio-Rad) 10%) was added in 5 volumes of the crushed gel, and the mixture was stirred at room temperature, to thereby elute the protein band. The eluate was dialyzed against ammonium acetate (2 mM) and was then lyophilized. The lyophilized sample was served to determine the N-terminal sequence for Protein Sequence type 476A (product of Applied Biosystem).

The obtained N-terminal sequences are shown in FIG. 7. (SEQ IDS NOS: 9–13).

20–30 Nucleotides primers (SEQ ID NOS: 14–20 for 5'-terminal of +chain and that of the −chain corresponding to the obtained N-terminal sequences were synthesized (SEQ ID NOS: 9–13). PCR reaction was carried out in a 100-μL reaction system by use of a template DNA (100 ng), a primer (20 pmol), and PwoDNA polymerase (product of Boehringer Mannheim). When inverse PCR was performed, Expand™ long template PCR system (product of Boehringer Mannheim) was used in a 50-μL reaction system. PCR carried out by use of these primers, 9860-N2 SEQ ID NO: 14) and 9860-25k-RV (SEQ ID NO: 17), provided a DNA fragment of 527 bp.

(4) Subcloning of the PCR Product

The PCR product was purified with a High Pure PCR Product Purification Kit (product of Boehringer Mannheim) and inserted to the Sma I site of pUC18 through overnight reaction at 16° C. with Ligation kit ver. 2 (product of Takara). The resultant recombinant plasmid and the competent cell E. coli JM109 strain (product of Takara) were mixed, and the mixture was subjected to heat shock (42° C., 45 seconds), to thereby transform the E. coli JM109 cells. LB was added to the cells. After being maintained at 37° C. for one hour, the mixture was applied to an LB plate containing IPTG (0.1 mM, Sigma), X-gal [0.004% (w/v), Sigma], and ampicillin (50 μg/mL, Sigma). Cultivation was performed overnight at 37° C., and grown white colonies were selected as transformants having the recombinant plasmid.

(5) Determination of the Nucleotide Sequence

The transformant was cultivated overnight at 37° C. in LB containing ampicillin (50 μg/mL), and cells were collected through centrifugation. The recombinant plasmid was obtained by use of High Pure Plasmid Isolation Kit (product of Boehringer Mannheim). PCR for sequencing was performed in a 20-μL reaction system by use of a primer and a DNA sequencing kit (product of PERKIN ELMER), the obtained recombinant plasmid (1 μg) was served as a template DNA. The reaction product was purified by use of Quick Spin Column (product of Boehringer mannheim), and dried up by use of a centrifugal evaporator. The thus-treated sample was subjected to analysis by use of DNA Sequencer Type 377 (product of Applied Biosystem).

The DNA fragment obtained through PCR had the amino acid sequence which matches the N-terminal sequence of the KP-9860 protease, and there were observed sequences, which match common sequences near Asp and His among three amino acids. (Asp, His, Ser) forming an active center of alkaline protease such as subtilisin. Thus, the DNA fragment was considered to be a portion of the KP-9860 protease gene.

(6) Southern Hybridization

KP9860 chromosome was treated with EcoR I, Sac I, Kpn I, Hind III, BamH I, Xho I, Pst I, and Bgl II. Southern hybridization was performed by use of the obtained 527 bp DNA as a probe, to thereby detect a complementary region.

As a result, hybridization bands were observed in the lanes other than the lane attributed to Kpn I.

(7) Inverse PCR

Figure 9:
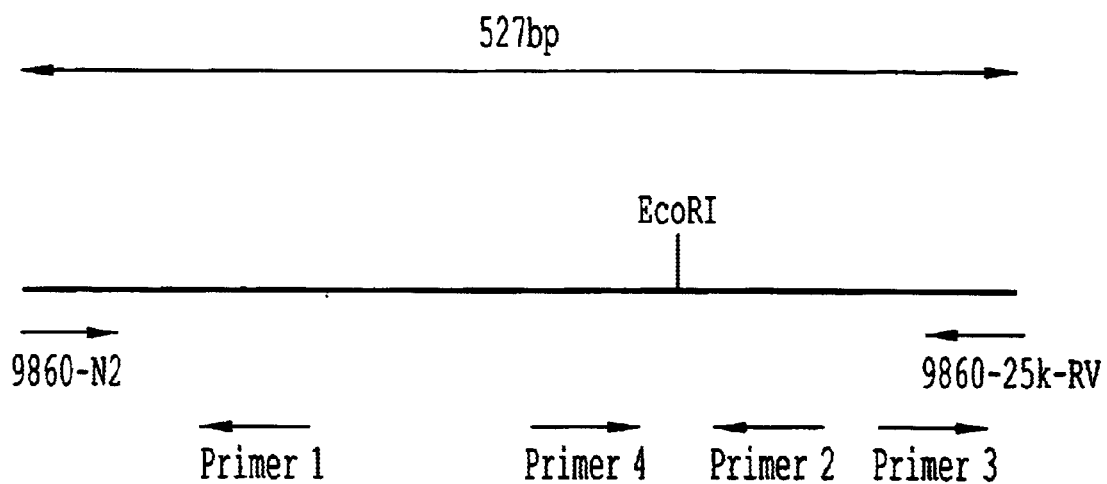
FIG. 9 shows 57 bp PCR-amplified fragments and primer designs (SEQ ID NOS:21–24).

Inverse PCR was performed by use of primers (1~4 (FIG. 9 (SEQ ID NOS: 21–24) Synthesized from the obtained 527 bp sequence. The KP-9860 chromosome was completely digested by use of restriction enzymes, i.e., EcoRI, HindIII, PstI, and BglII, and each sample was treated by use of Ligation Kit Ver. 2 (product of Takara)for circularization. Each of the resultant reaction mixtures was served as a template DNA for inverse PCR. PCR reaction (conditions; (94° C.-10 seconds, 60° C.-30 seconds, 68° C.-4 minutes)× 10 cycles; (94° C.-10 seconds, 60° C.-30 seconds, 68° C.-4 minutes+20×the number of cycles)×20 cycles; 68° C.-7 minutes; and 4° C.-1 minute) was performed by use of the template DNA described above (0.1 μg), primers 1 and 4 (10 pmol, respectively), and the Expand Long Plate PCR System. In addition, PCR (conditions; as described above) was performed by use of the template DNA derived from Eco RI digested chromosome (0.1 μg), primers 2 and 3 (10 pmol, respectively), and the Expand Long Plate PCR System. The resultant amplified DNA fragments were purified by use of High Pure PCR Product Purification Kit, and terminals were converted to blunt-ended by use of DNA Blunting Kit (product of Takara). Each of the obtained DNA fragments and SmaI digested pUC18 were mixed, and the mixture was treated with Ligation Kit Ver. 2. As described above, E. coli JM 109 strain was transformed by the recombinant plasmid, and the obtained recombinant plasmid was served as a template DNA for sequencing. Thus, the nucleotide sequence of the amplified DNA fragments was determined.

(8) Analysis of the Entire Nucleotide Sequence of the KP-9860 Protease Gene

The sequencing revealed that the KP-9860 protease gene contains an open reading frame (ORF) encoding the 1917 bp, 639 amino acid residues and that the ORF contains a region (NDVARHIVKADVAQSSYGLY)(SEQ ID NO: 9) which matches the N-terminal sequence of the purified KP9860 protease. Judging from the N-terminal sequence, the muture region of KP9860 protease gene was deduced to be the 1302 bp, encoding 434 amino acid residues (SEQ ID NO: 4), molecular weight 45310 Da). Upstream of the ORF, there were observed sequences which are deduced to be a promoter region (−35 region: ttgtgt, −10 region: tacgat) and a ribosome-binding site (SD sequence: aggagt). Downstream of the termination codon (taa), there was an inverted repeat having a free energy of −26.2 kcal/mol, which is deduced to be a terminator.

The procedure of Example 5 was repeated, to thereby analyze the entire nucleotide sequence and amino acid sequence of each of the genes of KP-43 protease and KP-1790 protease. The results are shown in SEQ ID NOS: 4 and 5.

Example 6

Washing Test

A washing test was carried out according to JIS K 3371. Detergents whose compositions are shown in Table 7 were dissolved in water containing 71.2 mg of $CaCO_3$/L (4° DH) so as to adjust the concentration, and each protease was added to detergent solution so as to adjust the concentration of the alkaline protease to 40 mAPU/L according to the Anson-Hemoglobin method (see Table 8).

Collars of shirts (worn for 3 days) were employed as specimens. For comparison, after the cloth of a collar was cut into a size of about 8×8 cm, the cloth was washed at 15° C. and 100 rpm, for 10 minutes by use of a Terg-O-Tometer (Ueshima Seisakusyo) with addition of the enzyme or without addition of the enzyme. After being rinsed and dried, pairs of collar clothes (15 pairs) were compared and evaluated by visual judgement. When the soil was almost completely cleaned, an evaluation of 5 was assigned, and when the soil was hardly cleaned, an evaluation of 1 was assigned, and the total scores of 15 specimens were calculated. The detergency index was expressed as the scores of each composition, with the detergency of a detergent composition without addition of the enzyme taken as 100. The results are shown in Table 8.

TABLE 7

| Compound (%) | (wt. %) | | |
|---|---|---|---|
| | Detergent A | Detergent B | Detergent C |
| LAS | 23.0 | 4.0 | 20.0 |
| AS | 4.0 | | |
| AE | 5.0 | | |
| AEP | | 5.0 | |
| AES | | 20.0 | |
| Fatty acid salt | 3.0 | 2.5 | 2.0 |
| Zeolite | 22.0 | 20.0 | |
| Sodium carbonate | 15.0 | | |
| Potassium carbonate | 3.0 | | |
| Amorphous silicate | 7.0 | | 7.0 |
| Crystalline silicate | 4.0 | | |
| Sodium sulfite | 2.0 | 0.5 | 2.0 |
| Sodium sulfate | 2.0 | | 23.0 |
| AA-MA | 5.0 | | |
| Citrate | | | 10.0 |
| PEG | 2.0 | | 2.0 |
| Monoethanolamine | | 8.0 | |
| Ethanol | | 5.0 | |
| Water | 3.0 | balance | 7.0 |
| Form | G* | L** | G* |

TABLE 7-continued

| Compound (%) | (wt. %) | | |
|---|---|---|---|
| | Detergent A | Detergent B | Detergent C |
| Concentration in use | 20g/30L | 20g/30L | 40g/30L |
| pH after washing | 10.7 | 9.2 | 8.0 |

*G stands for granular.
**L stands for liquid.
LAS: sodium linear alkyl(C12–C14)benzene sulfonate (free acid incorporated into a liquid detergent)
AS: alkyl sulfate
AE: polyoxyethylene lauryl ether (average EO addition of 4 moles)
AEP: polyoxyethylene polyoxypropylene lauryl ether (average EO addition of 8 mol, average PO addition of 3 mol)
AES: alkyl ether sulfate (average EO addition of 2.5 mol)
Fatty acid: palm oil-derived fatty acid sodium salt
Zeolite: zeolite 4A, average particle size of 3 μm
Sodium carbonate: dense ash
Amorphous silicate: JIS No. 2 sodium silicate
Crystalline silicate: pulverized SKS-6 (product of Hoechst Tokuyama), average particle size of 15 μm
AA-MA: Sokalan CP5, acrylic acid-maleic acid copolymer (product of BASF)
PEG: polyethylene glycol, average molecular weight of 8,000

TABLE 8

| | Protease | Detergency index Detergent A |
|---|---|---|
| Detergent of the invention 1 | Bacillus sp. KSM-KP43 (Example 2) | 106 |
| Detergent of the invention 2 | Bacillus sp. KSM-KP1790 (Example 3) | 106 |
| Detergent of the invention 3 | Bacillus sp. KSM-KP9860 (Example 3) | 105 |
| Comparative detergent 1 | Savinase 120T type White ® (Novo Nordisk) | 103.5 |
| Comparative detergent 2 | Durazym 6.0T ® (Novo Nordisk) | 103.5 |
| Comparative detergent 3 | None | 100 |

Table 8 demonstrates that, even under the same activity conditions, the detergent composition containing the enzyme of the present invention (detergent A) exhibits superior detergency as compared to detergents containing conventional proteases. Detergents B and C also exhibit excellent detergency of the present invention.

Example 7

A granular product was prepared through a method disclosed in Japanese Patent Application Laid-Open (kokai) No. 62-257990 by use of a purified sample of protease of the present invention which had been derived from Bacillus sp. KSM-KP43, KSM-KP1790, or KSM-KP9860 and prepared in Example 2 or 3. The granular product (6 APU/g) (1 part by weight) was incorporated into each of detergents (100 parts by weight) having compositions shown in Table 9, to thereby obtain detergent compositions of the present invention. When the detergent was of the granular type, such a detergent was prepared by blending a granular detergent base which is free of components; i.e., an enzyme, PC, AC-1, and AC-2, with a granulated enzyme, granulated PC, granulated AC-1, and granulated AC-2. Each detergent was dissolved in water containing 71.2 mg $CaCO_3$/L (4° DH) at a concentration for use, and a collar was washed in a manner as described in Example 6. The detergents produced herein exhibit excellent washing power, and are useful for a laundry detergent.

TABLE 9

| Component (%) | Detergents of the present invention | | | | | | | | | |
|---|---|---|---|---|---|---|---|---|---|---|
| | 4 | 5 | 6 | 7 | 8 | 9 | 10 | 11 | 12 | 13 |
| LAS-2 | 20 | | 20.5 | | 12 | | | | 5 | 10 |
| LAS-3 | | 15 | | | | | | | | |
| AS-2 | | | 5 | | 10 | | 20 | | | |
| SAS | 3 | | | | | | | | | |
| AOS | | 3 | | | | | | | | |
| SFE | | 8 | | | | | | | | |
| Fatty acid salt | 2 | 6 | 4 | 10 | 3 | 3 | 2 | 1.5 | | |
| AES-2 | | | | | | | | 20 | | |
| AE-3 | 3 | | | | | | | | | 10 |
| AE-4 | | 3 | 3 | 15 | | 15 | 3 | | 15 | |
| AE-5 | | | | | | | 2 | 20 | 20 | 25 |
| AG | | | | | | | | | 5 | 7 |
| Zeolite | 30 | 18 | 15 | 15 | | 10 | 20 | | | |
| Oil-absorbing carrier | | | | 10 | | 12 | | | | |
| Crystalline silicate | | | | 20 | | | | | | |
| Amorphous silicate | 12 | 1 | 8 | | 10 | | 5 | | | |
| STPP | | | | | 25.5 | 20 | | | | |
| Sodium carbonate | 10 | 27 | 25 | 10 | 10 | 15 | 17.5 | 0.1 | | |
| Potassium carbonate | | 3 | | 2 | 5 | | | | | |
| Sodium sulfite | 2 | 2 | | | 1 | | | 0.2 | 0.2 | 0.2 |
| Sodium sulfate | 4.5 | 1.5 | | 1 | 11 | 8 | 10 | | | |
| Sodium citrate | | | 4 | 2 | | | 5 | 1.5 | 1 | 1 |
| NTA | | | | | | 2 | | | | |
| Monoethanol-amine | | | | | | | | 4 | 5 | 6 |
| PAA | | | | | 1 | 1.5 | 3 | | | |
| AA-MA | | 3 | 3 | 5 | | | | | | |
| CMC | 2 | | | | | | | | | |
| PEG | 5 | 2 | 2 | 2 | 2 | | | 1.5 | | |
| PVP | | | | | | | 2 | | | |
| Fluorescent dye | 0.3 | 0.3 | 0.3 | 0.3 | 0.3 | 0.3 | 0.3 | 0.1 | 0.1 | 0.1 |
| Perfume | 0.2 | 0.2 | 0.2 | 0.2 | 0.2 | 0.2 | 0.2 | 0.3 | 0.3 | 0.3 |
| Water | 4 | 5 | 3 | 0.5 | 6 | 1 | 5 | 43.7 | 38.2 | 30.2 |
| Ethanol | | | | | | | | 5 | 5 | 5 |
| Propylene glycol | | | | | | | | 2 | 5 | 5 |
| Enzyme | 2 | 2 | 2 | 3 | 3 | 2 | 2 | 0.1 | 0.2 | 0.2 |
| PC | | | 3 | 3 | 10 | 3 | | | | |
| AC-1 | | | 2 | | | | | | | |
| AC-2 | | | | 1 | | | | | | |
| Total | 100 | 100 | 100 | 100 | 100 | 100 | 100 | 100 | 100 | 100 |
| Form | G* | G* | G* | G* | G* | G* | G* | L** | L** | L** |
| Concentration in use | 20 g/ 30 L | 20 g/ 30 L | 20 g/ 30 L | 20 g/ 30 L | 20 g/ 30 L | 20 g/ 30 L | 20 g/ 30 L | 20 mL/ 30 L | 20 mL/ 30 L | 20 mL/ 30 L |

*) G stands for granular.
**) L stands for liquid.
LSA-2: alkylbenzene sulfonic acid (C10–C14 alkyl chain) which was neutralized with 48% NaOH
LSA-3: alkylbenzene sulfonic acid (C10–C14 alkyl chain) which was neutralized with 50% NaOH
AS-2: sodium salt of Dovanol 25 sulfate (C12–C15 sulfate)
SAS: sodium C13–C18 alkane sulfonate
AOS: sodium α-olefin sulfonate
SFE: sodium salt of palm oil α-sulfofatty acid methyl ester
Fatty acid salt: sodium palmitate
AES-2: sodium polyoxyethylene alkyl (C12–C15) ether sulfate (average EO addition of 2 moles)
AE-3: EO adduct (average 3 moles) of C12–C13 alcohol
AE-4: EO adduct (average 7.2 moles) of C12–C15 alcohol
AE-5: EO adduct (average 7 moles) of C12–C15 secondary alcohol
AG: alkyl (palm oil-derived) glucoside (average polymerization degree of 1.5)
Oil-absorbing carrier: Amorphous sodium aluminosilicate, oil absorption of 235 mL/100 g
Crystalline silicate: SKS-6 (δ-$Na_2Si_2O_5$, crystalline layered silicate, average particle size of 20 μm)
Amorphous silicate: JIS No. 1 sodium silicate TABLE 9-continued

| Component | Detergents of the present invention | | | | | | | | | |
|---|---|---|---|---|---|---|---|---|---|---|
| (%) | 4 | 5 | 6 | 7 | 8 | 9 | 10 | 11 | 12 | 13 |

STPP: sodium tripolyphosphate
NTA: sodium nitrilotriacetate
PAA: sodium salt of poly(acrylic acid), average molecular weight of 12,000
AA-MA: acrylic acid/maleic acid copolymer
CMC: carboxymethyl cellulose sodium
PEG: polyethylene glycol, average molecular weight of 6,000
PVA: polyvinylpyrrolidone, average molecular weight of 40,000, K value of 26–35
Fluorescent dye: Tinopal CBS and Whitex SA (1:1 (wt.)), only Cinopearl incorporated into a liquid detergent
Perfume: A perfume composition disclosed in Japanese Patent Application Laid-Open (kokai) No. 8-239700
Enzyme: Lipolase 100T, Termamyl 60T, and KAC 500 ® (product of Kao Corporation) 1:1:1 (wt.)
PC: sodium percarbonate, average particle size of 400 μm, coated with sodium metaborate
AC-1: tetraacetylethylenediamine
AC-2: sodium lauroyloxybenzene sulfonate Example 8

Among the components shown in Table 10, sodium percarbonate and sodium carbonate (dense ash) were mixed with stirring. To the mixture, a 40% aqueous solution of sodium polyacrylate and sodium linear alkylbenzene sulfonate (or nonionic surfactant or sodium lauroyloxybenzene sulfonate) were added. Subsequently, a granulation product of alkaline protease which had been derived from Bacillus sp. KSM-KP43 and prepared in Example 7 was added to the mixture. The resultant mixture was homogeneously stirred, to thereby prepare a bleaching agent. A collar was immersed in a 0.5% aqueous solution of each of the bleaching agents at 20° C. for 30 minutes, and subsequently washed with detergent A (Example 6) in a Terg-O-Tometer at 100 rpm for 10 minutes at 20° C. The obtained bleaching agents have excellent bleaching ability, and are useful as a bleaching agent for laundry.

TABLE 10

(wt. %)

| | Bleaching agents of the present invention | | | |
|---|---|---|---|---|
| Component | 14 | 15 | 16 | 17 |
| Sodium percarbonate[1] | 80.0 | 80.0 | 80.0 | 80.0 |
| Sodium carbonate (dense ash) | 16.0 | 12.0 | 16.0 | 12.0 |
| Anionic surfactant[2] | 2.0 | 2.0 | — | — |
| Nonionic surfactant[3] | — | — | 2.0 | 2.0 |
| Sodium polyacrylate[4] | 1.0 | 1.0 | 1.0 | 1.0 |
| Sodium lauroyloxy-benzene sulfonate | — | 4.0 | — | 4.0 |
| Bacillus sp. KSM-KP43 Alkaline protease (Ex. 7) | 1.0 | 1.0 | 1.0 | 1.0 |

[1]Particle size: 500–700 μm
[2]Sodium linear alkylbenzene sulfonate (C12—C14)
[3]Polyoxyethylene alkyl ether (C12—C14 alkyl, average EO addition of 12 mol)
[4]Average molecular weight of 8,000

Example 9

The procedure of Example 8 was repeated, to thereby prepare detergent compositions for an automated dishwasher having a composition shown in Table 11. Washing power of the obtained compositions was tested under the following conditions. The obtained detergents have excellent washing power, and are useful as a detergent for an automated dishwasher.

TABLE 11

(wt. %)

| | Detergents of the present invention | | | |
|---|---|---|---|---|
| Component | 18 | 19 | 20 | 21 |
| Pluronic L-61[1] | 4 | — | 4 | 4 |
| Softanol EP-7085[2] | — | 4 | — | — |
| Trisodium citrate | 30 | 30 | — | — |
| EDTA | — | — | 30 | — |
| Sodium tripoly-phosfate | — | — | — | 30 |
| Sodium percarbonate | 20 | 20 | 20 | 20 |
| Sodium carbonate (dense ash) | 20 | 20 | 20 | 20 |
| Amorphous silicate[3] | 10 | 10 | 10 | 10 |
| AA-MA[4] | 4 | 4 | 4 | 4 |
| Sodium sulfate | 10 | 10 | 10 | 10 |
| Lipolase 100T ® (Novo Nordisk) | 0.5 | 0.5 | 0.5 | 0.5 |
| Termamyl 60T ® (Novo. Nordisk) | 1 | 1 | 1 | 1 |
| Bacillus sp. KSM-KP43 alkaline protease (Ex.7) | 0.5 | 0.5 | 0.5 | 0.5 |

[1]Polyoxyethylene-polyoxypropylene copolymer (average molecular weight of 2,000)
[2]Ethylene oxide (7 moles) and propylene oxide (8.5 moles) adduct of C12—C14 sec-alcohol
[3]JIS No. 2 sodium silicate
[4]Acrylic acid-maleic acid copolymer (1) Preparation of a Soiled Dish
Egg yolk (2.5 g) was homogeneously brushed onto one ceramic dish having a diameter of 25 cm. The dish was dried in a drier at 115° C. for 60 minutes.
(2) Washing Conditions
  Washer used; Full automated dishwasher (NP-810, product of Matsushita Electric Industry Co., Ltd.)
  Type of washing; Standard course
  Water for washing; Hardness of 62.3 mg CaCO₃/L (3.5° DH)
  Concentration of detergent; 0.2 wt. %
(3) Method for Evaluation
Five soiled dishes were washed in the washer under the above conditions by use of the detergent compositions of Example 9. The washed dish was stained with a 1% Erythrosine solution, to thereby color residual protein. The degree of protein soil was judged visually.

Example 10

Detergent compositions for an automated dishwasher were obtained from components shown in Table 12. Washing power of these compositions were evaluated through a test similar to that of Example 9. The compositions provided an excellent washing effect.

TABLE 12

(wt. %)

Detergent compositions of the present invention

| Component | 22 | 23 | 24 | 25 | 26 |
|---|---|---|---|---|---|
| (a) Sodium carbonate | 30 | | 30 | | 50 |
| Sodium hydrogen-carbonate | | 25 | | 25 | |
| (b) Sokalan CP5[1) | 5 | 6 | 5 | 5 | 5 |
| (c) Sodium hydrogen-percarbonate | 5 | | 6 | | |
| (d) Limonene | 2 | 2 | | 1 | 1 |
| Softanol EP7045[2) | | | 2 | 1 | 1 |
| (e) Amorphous sodium aluminosilicate (Synth. Ex.1)[3) | 2 | | 2 | 1 | 3 |
| Amorphous sodium aluminosilicate (Synth. Ex. 2)[4) | | 2 | | 1 | |
| Lipolase 100T ® (Novo Nordisk) | 0.5 | 0.5 | 0.5 | 0.5 | 0.5 |
| Termamyl 60T ® (Novo Nordisk) | 1 | 1 | 1 | 1 | 1 |
| *Bacillus sp.* KSM-KP43 alkaline protease (Ex. 7) | 0.5 | 0.5 | 0.5 | 0.5 | 0.5 |
| Sodium malate | | 10 | | 5 | |
| Sodium citrate | 15 | | 10 | 4 | 8 |
| Sodium sulfate | 39 | 53 | 43 | 55 | 30 |

[1)Acrylic acid/maleic acid copolymer (product of BASF)
[2)Ethylene oxide (7 moles) and propylene oxide (4.5 moles) adduct of C12–C14 sec-alcohol
[3), [4)Synthetic Example disclosed in Japanese Patent Application Laid-Open (kokai) No. 6-179899

Example 11

Enzymes were added to the above-described detergent A (Example 6) in amounts shown in the following Table 13. A collar portion of a white shirt was washed in a manner similar to that of Example 6.

TABLE 13

(wt. %)

Detergents of the present invention

| Enzyme | 27 | 28 | 29 | 30 | 31 | 32 | 33 |
|---|---|---|---|---|---|---|---|
| Protease of the present invention[1) | — | 0.5 | 0.5 | 0.5 | 0.5 | 0.5 | 0.5 |
| Conventional protease[2) | — | — | 0.6 | — | — | 0.6 | 0.6 |
| Cellulase[3) | — | — | — | 0.7 | — | 0.7 | 0.7 |
| Lipase[4) | — | — | — | — | 0.5 | — | 0.5 |

[1)A granular product prepared through a method disclosed in Japanese Patent Application Laid-Open (kokai) No. 62-257990 by use of a purified sample of protease of the present invention which was derived from *Bacillus sp.* KSM-KP 43 strain and prepared in Example 2 (6 APU/g)
[2)Protease K-16 disclosed in Japanese Patent Application Laid-Open (kokai) No. 5-25492 which was modified to have 5 APU/g through a method disclosed in Japanese Patent Application Laid-Open (kokai) No. 62-257990
[3)KAC-500 ® (cellulase, 500 U/g, product of Kao Corporation)
[4)Lipolase 100T ® (product of Novo Nordisk)

---

What is claimed is:

1. An isolated alkaline protease having an amino acid sequence which is at least 90% homologous to an amino acid sequence selected from the group consisting of SEQ ID NO: 1 and SEQ ID NO: 2, wherein said isolated alkaline protease has alkaline protease activity.

2. The alkaline protease of claim 1, which has an amino acid sequence that is at least 90% homologous to the amino acid sequence of SEQ ID NO: 1.

3. A detergent composition comprising the alkaline protease of claim 2.

4. The detergent composition of claim 3, which contains 0.1 to 5000 U of the alkaline protease per kg of the composition.

5. The detergent composition of claim 4, which comprises a surfactant.

6. The detergent composition of claim 4, which comprises 0.5 to 60 wt. % of the detergent.

7. The detergent composition of claim 4, which contains at least one enzyme other than the alkaline protease.

8. The alkaline protease of claim 1, which has an amino acid sequence that is at least 90% homologous to the amino acid sequence of SEQ ID NO: 2.

9. A detergent composition comprising the alkaline protease of claim 8.

10. The detergent composition of claim 9, which contains 0.1 to 5000 U of the alkaline protease per kg of the composition.

11. The detergent composition of claim 10, which comprises a surfactant.

12. The detergent composition of claim 10, which comprises 0.5 to 60 wt. % of the detergent.

13. The detergent composition of claim 10, which contains at least one enzyme other than the alkaline protease.

14. The alkaline protease of claim 1, wherein said alkaline protease has the following physicochemical properties:

(i) Acting pH range acting over a wide pH range of 4–13 and exhibiting, at a pH of 6–12, 80% or more of the activity at the optimum pH;

(ii) Stable pH range being stable over a pH range of 6–11 when treated at 40° C. for 30 minutes;

(iii) Isoelectric point having an isoelectric point of approximately 8.9–9.1; and (iv) Effect of a fatty acid casein-degrading activity not being inhibited by oleic acid.

* * * * *

SEQUENCE LISTING

```
<160> NUMBER OF SEQ ID NOS: 24

<210> SEQ ID NO 1
<211> LENGTH: 639
<212> TYPE: PRT
<213> ORGANISM: Bacillus sp.
<220> FEATURE:
<221> NAME/KEY: misc_feature
<222> LOCATION: (23)..(23)
<223> OTHER INFORMATION: Xaa is any amino acid
<221> NAME/KEY: misc_feature
<222> LOCATION: (29)..(29)
<223> OTHER INFORMATION: Xaa is any amino acid
<221> NAME/KEY: misc_feature
<222> LOCATION: (32)..(32)
<223> OTHER INFORMATION: Xaa is any amino acid
<221> NAME/KEY: misc_feature
<222> LOCATION: (46)..(46)
<223> OTHER INFORMATION: Xaa is any amino acid
<221> NAME/KEY: misc_feature
<222> LOCATION: (47)..(47)
<223> OTHER INFORMATION: Xaa is any amino acid
<221> NAME/KEY: misc_feature
<222> LOCATION: (53)..(53)
<223> OTHER INFORMATION: Xaa is any amino acid
<221> NAME/KEY: misc_feature
<222> LOCATION: (70)..(70)
<223> OTHER INFORMATION: Xaa is any amino acid
<221> NAME/KEY: misc_feature
<222> LOCATION: (74)..(74)
<223> OTHER INFORMATION: Xaa is any amino acid
<221> NAME/KEY: misc_feature
<222> LOCATION: (89)..(89)
```

```
<223> OTHER INFORMATION: Xaa is any amino acid
<221> NAME/KEY: misc_feature
<222> LOCATION: (102)..(102)
<223> OTHER INFORMATION: Xaa is any amino acid
<221> NAME/KEY: misc_feature
<222> LOCATION: (105)..(105)
<223> OTHER INFORMATION: Xaa is any amino acid
<221> NAME/KEY: misc_feature
<222> LOCATION: (128)..(128)
<223> OTHER INFORMATION: Xaa is any amino acid
<221> NAME/KEY: misc_feature
<222> LOCATION: (130)..(130)
<223> OTHER INFORMATION: Xaa is any amino acid
<221> NAME/KEY: misc_feature
<222> LOCATION: (131)..(131)
<223> OTHER INFORMATION: Xaa is any amino acid
<221> NAME/KEY: misc_feature
<222> LOCATION: (132)..(132)
<223> OTHER INFORMATION: Xaa is any amino acid
<221> NAME/KEY: misc_feature
<222> LOCATION: (133)..(133)
<223> OTHER INFORMATION: Xaa is any amino acid
<221> NAME/KEY: misc_feature
<222> LOCATION: (146)..(146)
<223> OTHER INFORMATION: Xaa is any amino acid
<221> NAME/KEY: misc_feature
<222> LOCATION: (148)..(148)
<223> OTHER INFORMATION: Xaa is any amino acid
<221> NAME/KEY: misc_feature
<222> LOCATION: (160)..(160)
<223> OTHER INFORMATION: Xaa is any amino acid
<221> NAME/KEY: misc_feature
<222> LOCATION: (165)..(165)
<223> OTHER INFORMATION: Xaa is any amino acid
<221> NAME/KEY: misc_feature
<222> LOCATION: (172)..(172)
<223> OTHER INFORMATION: Xaa is any amino acid
<221> NAME/KEY: misc_feature
<222> LOCATION: (183)..(183)
<223> OTHER INFORMATION: Xaa is any amino acid
<221> NAME/KEY: misc_feature
<222> LOCATION: (187)..(187)
<223> OTHER INFORMATION: Xaa is any amino acid
<221> NAME/KEY: misc_feature
<222> LOCATION: (188)..(188)
<223> OTHER INFORMATION: Xaa is any amino acid
<221> NAME/KEY: misc_feature
<222> LOCATION: (189)..(189)
<223> OTHER INFORMATION: Xaa is any amino acid
<221> NAME/KEY: misc_feature
<222> LOCATION: (194)..(194)
<223> OTHER INFORMATION: Xaa is any amino acid
<221> NAME/KEY: misc_feature
<222> LOCATION: (286)..(286)
<223> OTHER INFORMATION: Xaa is any amino acid
<221> NAME/KEY: misc_feature
<222> LOCATION: (306)..(306)
<223> OTHER INFORMATION: Xaa is any amino acid
<221> NAME/KEY: misc_feature
<222> LOCATION: (324)..(324)
<223> OTHER INFORMATION: Xaa is any amino acid
<221> NAME/KEY: misc_feature
<222> LOCATION: (369)..(369)
<223> OTHER INFORMATION: Xaa is any amino acid
<221> NAME/KEY: misc_feature
<222> LOCATION: (431)..(431)
<223> OTHER INFORMATION: Xaa is any amino acid
<221> NAME/KEY: misc_feature
<222> LOCATION: (501)..(501)
<223> OTHER INFORMATION: Xaa is any amino acid
<221> NAME/KEY: misc_feature
<222> LOCATION: (531)..(531)
<223> OTHER INFORMATION: Xaa is any amino acid
<221> NAME/KEY: misc_feature
<222> LOCATION: (541)..(541)
<223> OTHER INFORMATION: Xaa is any amino acid
<221> NAME/KEY: misc_feature
<222> LOCATION: (584)..(584)
<223> OTHER INFORMATION: Xaa is any amino acid
```

-continued

```
<221> NAME/KEY: misc_feature
<222> LOCATION: (591)..(591)
<223> OTHER INFORMATION: Xaa is any amino acid
<221> NAME/KEY: misc_feature
<222> LOCATION: (592)..(592)
<223> OTHER INFORMATION: Xaa is any amino acid
<221> NAME/KEY: misc_feature
<222> LOCATION: (594)..(594)
<223> OTHER INFORMATION: Xaa is any amino acid
<221> NAME/KEY: misc_feature
<222> LOCATION: (595)..(595)
<223> OTHER INFORMATION: Xaa is any amino acid
<221> NAME/KEY: misc_feature
<222> LOCATION: (596)..(596)
<223> OTHER INFORMATION: Xaa is any amino acid
<221> NAME/KEY: misc_feature
<222> LOCATION: (611)..(611)
<223> OTHER INFORMATION: Xaa is any amino acid
<221> NAME/KEY: misc_feature
<222> LOCATION: (632)..(632)
<223> OTHER INFORMATION: Xaa is any amino acid

<400> SEQUENCE: 1

Met Arg Lys Lys Lys Val Phe Leu Ser Val Leu Ser Ala Ala Ala Ile
1               5                   10                  15

Leu Ser Thr Val Ala Leu Xaa Asn Pro Ser Ala Gly Xaa Ala Arg Xaa
            20                  25                  30

Phe Asp Leu Asp Phe Lys Gly Ile Gln Thr Thr Thr Asp Xaa Xaa Gly
        35                  40                  45

Phe Ser Lys Gln Xaa Gln Thr Gly Ala Ala Phe Leu Val Glu Ser
    50                  55                  60

Glu Asn Val Lys Leu Xaa Lys Gly Leu Xaa Lys Lys Leu Glu Thr Val
65                  70                  75                  80

Pro Ala Asn Asn Lys Leu His Ile Xaa Gln Phe Asn Gly Pro Ile Leu
                85                  90                  95

Glu Glu Thr Lys Gln Xaa Leu Glu Xaa Thr Gly Ala Lys Ile Leu Asp
            100                 105                 110

Tyr Ile Pro Asp Tyr Ala Tyr Ile Val Glu Tyr Glu Gly Asp Val Xaa
        115                 120                 125

Ser Xaa Xaa Xaa Xaa Ile Glu His Val Glu Ser Val Glu Pro Tyr Leu
    130                 135                 140

Pro Xaa Tyr Xaa Ile Asp Pro Gln Leu Phe Thr Lys Gly Ala Ser Xaa
145                 150                 155                 160

Leu Val Lys Ala Xaa Ala Leu Asp Thr Lys Gln Xaa Asn Lys Glu Val
                165                 170                 175

Gln Leu Arg Gly Ile Glu Xaa Ile Ala Gln Xaa Xaa Xaa Ser Asn Asp
            180                 185                 190

Val Xaa Tyr Ile Thr Ala Lys Pro Glu Tyr Lys Val Met Asn Asp Val
    195                 200                 205

Ala Arg Gly Ile Val Lys Ala Asp Val Ala Gln Ser Ser Tyr Gly Leu
210                 215                 220

Tyr Gly Gln Gly Gln Ile Val Ala Val Ala Asp Thr Gly Leu Asp Thr
225                 230                 235                 240

Gly Arg Asn Asp Ser Ser Met His Glu Ala Phe Arg Gly Lys Ile Thr
                245                 250                 255

Ala Leu Tyr Ala Leu Gly Arg Thr Asn Asn Ala Asn Asp Thr Asn Gly
            260                 265                 270

His Gly Thr His Val Ala Gly Ser Val Leu Gly Asn Gly Xaa Thr Asn
        275                 280                 285

Lys Gly Met Ala Pro Gln Ala Asn Leu Val Phe Gln Ser Ile Met Asp
```

```
                    290             295             300
Ser Xaa Gly Gly Leu Gly Leu Pro Ser Asn Leu Gln Thr Leu Phe
305                 310             315                 320

Ser Gln Ala Xaa Ser Ala Gly Ala Arg Ile His Thr Asn Ser Trp Gly
                325             330                 335

Ala Ala Val Asn Gly Ala Tyr Thr Thr Asp Ser Arg Asn Val Asp Asp
                340             345             350

Tyr Val Arg Lys Asn Asp Met Thr Ile Leu Phe Ala Ala Gly Asn Glu
            355             360             365

Xaa Pro Asn Gly Gly Thr Ile Ser Ala Pro Gly Thr Ala Lys Asn Ala
370             375             380

Ile Thr Val Gly Ala Thr Glu Asn Leu Arg Pro Ser Phe Gly Ser Tyr
385             390             395             400

Ala Asp Asn Ile Asn His Val Ala Gln Phe Ser Ser Arg Gly Pro Thr
                405             410             415

Lys Asp Gly Arg Ile Lys Pro Asp Val Met Ala Pro Gly Thr Xaa Ile
            420             425             430

Leu Ser Ala Arg Ser Ser Leu Ala Pro Asp Ser Ser Phe Trp Ala Asn
            435             440             445

His Asp Ser Lys Tyr Ala Tyr Met Gly Gly Thr Ser Met Ala Thr Pro
        450             455             460

Ile Val Ala Gly Asn Val Ala Gln Leu Arg Glu His Phe Val Lys Asn
465             470             475             480

Arg Gly Ile Thr Pro Lys Pro Ser Leu Leu Lys Ala Ala Leu Ile Ala
                485             490             495

Gly Ala Ala Asp Xaa Gly Leu Gly Tyr Pro Asn Gly Asn Gln Gly Trp
            500             505             510

Gly Arg Val Thr Leu Asp Lys Ser Leu Asn Val Ala Tyr Val Asn Glu
        515             520             525

Ser Ser Xaa Leu Ser Thr Ser Gln Lys Ala Thr Tyr Xaa Phe Thr Ala
        530             535             540

Thr Ala Gly Lys Pro Leu Lys Ile Ser Leu Val Trp Ser Asp Ala Pro
545             550             555             560

Ala Ser Thr Thr Ala Ser Val Thr Leu Val Asn Asp Leu Asp Leu Val
                565             570             575

Ile Thr Ala Pro Asn Gly Thr Xaa Tyr Val Gly Asn Asp Phe Xaa Xaa
            580             585             590

Pro Xaa Xaa Xaa Asn Trp Asp Gly Arg Asn Asn Val Glu Asn Val Phe
        595             600             605

Ile Asn Xaa Pro Gln Ser Gly Thr Tyr Thr Ile Glu Val Gln Ala Tyr
610             615             620

Asn Val Pro Val Gly Pro Gln Xaa Phe Ser Leu Ala Ile Val Asn
625             630             635

<210> SEQ ID NO 2
<211> LENGTH: 640
<212> TYPE: PRT
<213> ORGANISM: Bacillus sp.
<220> FEATURE:
<221> NAME/KEY: misc_feature
<222> LOCATION: (3)..(3)
<223> OTHER INFORMATION: Xaa is any amino acid
<221> NAME/KEY: misc_feature
<222> LOCATION: (24)..(24)
<223> OTHER INFORMATION: Xaa is any amino acid
<221> NAME/KEY: misc_feature
<222> LOCATION: (30)..(30)
```

```
<223> OTHER INFORMATION: Xaa is any amino acid
<221> NAME/KEY: misc_feature
<222> LOCATION: (33)..(33)
<223> OTHER INFORMATION: Xaa is any amino acid
<221> NAME/KEY: misc_feature
<222> LOCATION: (47)..(47)
<223> OTHER INFORMATION: Xaa is any amino acid
<221> NAME/KEY: misc_feature
<222> LOCATION: (48)..(48)
<223> OTHER INFORMATION: Xaa is any amino acid
<221> NAME/KEY: misc_feature
<222> LOCATION: (54)..(54)
<223> OTHER INFORMATION: Xaa is any amino acid
<221> NAME/KEY: misc_feature
<222> LOCATION: (71)..(71)
<223> OTHER INFORMATION: Xaa is any amino acid
<221> NAME/KEY: misc_feature
<222> LOCATION: (75)..(75)
<223> OTHER INFORMATION: Xaa is any amino acid
<221> NAME/KEY: misc_feature
<222> LOCATION: (90)..(90)
<223> OTHER INFORMATION: Xaa is any amino acid
<221> NAME/KEY: misc_feature
<222> LOCATION: (103)..(103)
<223> OTHER INFORMATION: Xaa is any amino acid
<221> NAME/KEY: misc_feature
<222> LOCATION: (106)..(106)
<223> OTHER INFORMATION: Xaa is any amino acid
<221> NAME/KEY: misc_feature
<222> LOCATION: (129)..(129)
<223> OTHER INFORMATION: Xaa is any amino acid
<221> NAME/KEY: misc_feature
<222> LOCATION: (131)..(131)
<223> OTHER INFORMATION: Xaa is any amino acid
<221> NAME/KEY: misc_feature
<222> LOCATION: (132)..(132)
<223> OTHER INFORMATION: Xaa is any amino acid
<221> NAME/KEY: misc_feature
<222> LOCATION: (133)..(133)
<223> OTHER INFORMATION: Xaa is any amino acid
<221> NAME/KEY: misc_feature
<222> LOCATION: (134)..(134)
<223> OTHER INFORMATION: Xaa is any amino acid
<221> NAME/KEY: misc_feature
<222> LOCATION: (147)..(147)
<223> OTHER INFORMATION: Xaa is any amino acid
<221> NAME/KEY: misc_feature
<222> LOCATION: (149)..(149)
<223> OTHER INFORMATION: Xaa is any amino acid
<221> NAME/KEY: misc_feature
<222> LOCATION: (161)..(161)
<223> OTHER INFORMATION: Xaa is any amino acid
<221> NAME/KEY: misc_feature
<222> LOCATION: (166)..(166)
<223> OTHER INFORMATION: Xaa is any amino acid
<221> NAME/KEY: misc_feature
<222> LOCATION: (173)..(173)
<223> OTHER INFORMATION: Xaa is any amino acid
<221> NAME/KEY: misc_feature
<222> LOCATION: (184)..(184)
<223> OTHER INFORMATION: Xaa is any amino acid
<221> NAME/KEY: misc_feature
<222> LOCATION: (188)..(188)
<223> OTHER INFORMATION: Xaa is any amino acid
<221> NAME/KEY: misc_feature
<222> LOCATION: (189)..(189)
<223> OTHER INFORMATION: Xaa is any amino acid
<221> NAME/KEY: misc_feature
<222> LOCATION: (190)..(190)
<223> OTHER INFORMATION: Xaa is any amino acid
<221> NAME/KEY: misc_feature
<222> LOCATION: (195)..(195)
<223> OTHER INFORMATION: Xaa is any amino acid
<221> NAME/KEY: misc_feature
<222> LOCATION: (287)..(287)
<223> OTHER INFORMATION: Xaa is any amino acid
<221> NAME/KEY: misc_feature
<222> LOCATION: (307)..(307)
<223> OTHER INFORMATION: Xaa is any amino acid
```

```
<221> NAME/KEY: misc_feature
<222> LOCATION: (325)..(325)
<223> OTHER INFORMATION: Xaa is any amino acid
<221> NAME/KEY: misc_feature
<222> LOCATION: (370)..(370)
<223> OTHER INFORMATION: Xaa is any amino acid
<221> NAME/KEY: misc_feature
<222> LOCATION: (432)..(432)
<223> OTHER INFORMATION: Xaa is any amino acid
<221> NAME/KEY: misc_feature
<222> LOCATION: (502)..(502)
<223> OTHER INFORMATION: Xaa is any amino acid
<221> NAME/KEY: misc_feature
<222> LOCATION: (532)..(532)
<223> OTHER INFORMATION: Xaa is any amino acid
<221> NAME/KEY: misc_feature
<222> LOCATION: (542)..(542)
<223> OTHER INFORMATION: Xaa is any amino acid
<221> NAME/KEY: misc_feature
<222> LOCATION: (585)..(585)
<223> OTHER INFORMATION: Xaa is any amino acid
<221> NAME/KEY: misc_feature
<222> LOCATION: (592)..(592)
<223> OTHER INFORMATION: Xaa is any amino acid
<221> NAME/KEY: misc_feature
<222> LOCATION: (593)..(593)
<223> OTHER INFORMATION: Xaa is any amino acid
<221> NAME/KEY: misc_feature
<222> LOCATION: (595)..(595)
<223> OTHER INFORMATION: Xaa is any amino acid
<221> NAME/KEY: misc_feature
<222> LOCATION: (596)..(596)
<223> OTHER INFORMATION: Xaa is any amino acid
<221> NAME/KEY: misc_feature
<222> LOCATION: (597)..(597)
<223> OTHER INFORMATION: Xaa is any amino acid
<221> NAME/KEY: misc_feature
<222> LOCATION: (612)..(612)
<223> OTHER INFORMATION: Xaa is any amino acid
<221> NAME/KEY: misc_feature
<222> LOCATION: (633)..(633)
<223> OTHER INFORMATION: Xaa is any amino acid

<400> SEQUENCE: 2

Met Arg Xaa Lys Lys Val Phe Leu Ser Val Leu Ser Ala Ala Ala
 1               5                  10                  15

Ile Leu Ser Thr Val Ala Leu Xaa Asn Pro Ser Ala Gly Xaa Ala Arg
            20                  25                  30

Xaa Phe Asp Leu Asp Phe Lys Gly Ile Gln Thr Thr Thr Asp Xaa Xaa
        35                  40                  45

Gly Phe Ser Lys Gln Xaa Gln Thr Gly Ala Ala Ala Phe Leu Val Glu
    50                  55                  60

Ser Glu Asn Val Lys Leu Xaa Lys Gly Leu Xaa Lys Lys Leu Glu Thr
65                  70                  75                  80

Val Pro Ala Asn Asn Lys Leu His Ile Xaa Gln Phe Asn Gly Pro Ile
                85                  90                  95

Leu Glu Glu Thr Lys Gln Xaa Leu Glu Xaa Thr Gly Ala Lys Ile Leu
            100                 105                 110

Asp Tyr Ile Pro Asp Tyr Ala Tyr Ile Val Glu Tyr Glu Gly Asp Val
        115                 120                 125

Xaa Ser Xaa Xaa Xaa Xaa Ile Glu His Val Glu Ser Val Glu Pro Tyr
130                 135                 140

Leu Pro Xaa Tyr Xaa Ile Asp Pro Gln Leu Phe Thr Lys Gly Ala Ser
145                 150                 155                 160

Xaa Leu Val Lys Ala Xaa Ala Leu Asp Thr Lys Gln Xaa Asn Lys Glu
            165                 170                 175

Val Gln Leu Arg Gly Ile Glu Xaa Ile Ala Gln Xaa Xaa Xaa Ser Asn
```

-continued

```
              180                 185                 190
Asp Val Xaa Tyr Ile Thr Ala Lys Pro Glu Tyr Lys Val Met Asn Asp
            195                 200                 205
Val Ala Arg Gly Ile Val Lys Ala Asp Val Ala Gln Ser Ser Tyr Gly
210                 215                 220
Leu Tyr Gly Gln Gly Gln Ile Val Ala Val Ala Asp Thr Gly Leu Asp
225                 230                 235                 240
Thr Gly Arg Asn Asp Ser Ser Met His Glu Ala Phe Arg Gly Lys Ile
                245                 250                 255
Thr Ala Leu Tyr Ala Leu Gly Arg Thr Asn Asn Ala Asn Asp Thr Asn
            260                 265                 270
Gly His Gly Thr His Val Ala Gly Ser Val Leu Gly Asn Gly Xaa Thr
            275                 280                 285
Asn Lys Gly Met Ala Pro Gln Ala Asn Leu Val Phe Gln Ser Ile Met
            290                 295                 300
Asp Ser Xaa Gly Gly Leu Gly Gly Leu Pro Ser Asn Leu Gln Thr Leu
305                 310                 315                 320
Phe Ser Gln Ala Xaa Ser Ala Gly Ala Arg Ile His Thr Asn Ser Trp
                325                 330                 335
Gly Ala Ala Val Asn Gly Ala Tyr Thr Thr Asp Ser Arg Asn Val Asp
            340                 345                 350
Asp Tyr Val Arg Lys Asn Asp Met Thr Ile Leu Phe Ala Ala Gly Asn
            355                 360                 365
Glu Xaa Pro Asn Gly Gly Thr Ile Ser Ala Pro Gly Thr Ala Lys Asn
            370                 375                 380
Ala Ile Thr Val Gly Ala Thr Glu Asn Leu Arg Pro Ser Phe Gly Ser
385                 390                 395                 400
Tyr Ala Asp Asn Ile Asn His Val Ala Gln Phe Ser Ser Arg Gly Pro
                405                 410                 415
Thr Lys Asp Gly Arg Ile Lys Pro Asp Val Met Ala Pro Gly Thr Xaa
            420                 425                 430
Ile Leu Ser Ala Arg Ser Ser Leu Ala Pro Asp Ser Ser Phe Trp Ala
            435                 440                 445
Asn His Asp Ser Lys Tyr Ala Tyr Met Gly Gly Thr Ser Met Ala Thr
            450                 455                 460
Pro Ile Val Ala Gly Asn Val Ala Gln Leu Arg Glu His Phe Val Lys
465                 470                 475                 480
Asn Arg Gly Ile Thr Pro Lys Pro Ser Leu Leu Lys Ala Ala Leu Ile
                485                 490                 495
Ala Gly Ala Ala Asp Xaa Gly Leu Gly Tyr Pro Asn Gly Asn Gln Gly
            500                 505                 510
Trp Gly Arg Val Thr Leu Asp Lys Ser Leu Asn Val Ala Tyr Val Asn
            515                 520                 525
Glu Ser Ser Xaa Leu Ser Thr Ser Gln Lys Ala Thr Tyr Xaa Phe Thr
            530                 535                 540
Ala Thr Ala Gly Lys Pro Leu Lys Ile Ser Leu Val Trp Ser Asp Ala
545                 550                 555                 560
Pro Ala Ser Thr Thr Ala Ser Val Thr Leu Val Asn Asp Leu Asp Leu
                565                 570                 575
Val Ile Thr Ala Pro Asn Gly Thr Xaa Tyr Val Gly Asn Asp Phe Xaa
            580                 585                 590
Xaa Pro Xaa Xaa Xaa Asn Trp Asp Gly Arg Asn Asn Val Glu Asn Val
            595                 600                 605
```

```
Phe Ile Asn Xaa Pro Gln Ser Gly Thr Tyr Thr Ile Glu Val Gln Ala
    610                 615                 620

Tyr Asn Val Pro Val Gly Pro Gln Xaa Phe Ser Leu Ala Ile Val Asn
625                 630                 635                 640

<210> SEQ ID NO 3
<211> LENGTH: 1920
<212> TYPE: DNA
<213> ORGANISM: Bacillus sp.
<220> FEATURE:
<221> NAME/KEY: CDS
<222> LOCATION: (1)..(1920)

<400> SEQUENCE: 3 atg aga aag aag aag gtg ttt tta tct gtt tta tca gct gca gcg att     48
Met Arg Lys Lys Lys Val Phe Leu Ser Val Leu Ser Ala Ala Ala Ile
1               5                   10                  15 ctg tcg act gtt gca tta aac aat ccc tcg gct ggt gat gca agg act    96
Leu Ser Thr Val Ala Leu Asn Asn Pro Ser Ala Gly Asp Ala Arg Thr
            20                  25                  30 ttt gat ctg gat ttt aaa gga att caa aca aca acc gat gtc agt ggt    144
Phe Asp Leu Asp Phe Lys Gly Ile Gln Thr Thr Thr Asp Val Ser Gly
        35                  40                  45 ttc tcc aaa cag cga caa aca ggt gcg gct gca ttt ctg gtg gag tct    192
Phe Ser Lys Gln Arg Gln Thr Gly Ala Ala Ala Phe Leu Val Glu Ser
    50                  55                  60 gaa aat gtg aaa ctt ctt aaa gga ttg cta aag aaa ctt gaa aca gta    240
Glu Asn Val Lys Leu Leu Lys Gly Leu Leu Lys Lys Leu Glu Thr Val
65                  70                  75                  80 ccg gca aat aat aaa ctc cat att gtc caa ttc aat ggc ccc att tta    288
Pro Ala Asn Asn Lys Leu His Ile Val Gln Phe Asn Gly Pro Ile Leu
                85                  90                  95 gaa gaa aca aaa cag aag cta gag aca act gga gca aag att ctc gac    336
Glu Glu Thr Lys Gln Lys Leu Glu Thr Thr Gly Ala Lys Ile Leu Asp
            100                 105                 110 tac atc cct gat tat gca tat att gtc gag tat gag ggg gat gtt cag    384
Tyr Ile Pro Asp Tyr Ala Tyr Ile Val Glu Tyr Glu Gly Asp Val Gln
        115                 120                 125 tca aaa gtc cgc tcc att gaa cac gtg gaa tca gtg gag cca tac ttg    432
Ser Lys Val Arg Ser Ile Glu His Val Glu Ser Val Glu Pro Tyr Leu
    130                 135                 140 ccg aaa tac aaa ata gat ccc cag ctt ttc aca aaa ggc gca tcg acg    480
Pro Lys Tyr Lys Ile Asp Pro Gln Leu Phe Thr Lys Gly Ala Ser Thr
145                 150                 155                 160 ctg gtg aaa gcg ttg gcg ctt gat acg aag cag aac aat aaa gaa gtg    528
Leu Val Lys Ala Leu Ala Leu Asp Thr Lys Gln Asn Asn Lys Glu Val
                165                 170                 175 caa tta aga ggc atc gag gaa atc gct cag tac gta gca agc aat gac    576
Gln Leu Arg Gly Ile Glu Glu Ile Ala Gln Tyr Val Ala Ser Asn Asp
            180                 185                 190 gtc cat tat att acg gca aag cct gaa tat aag gtg atg aat gat gtg    624
Val His Tyr Ile Thr Ala Lys Pro Glu Tyr Lys Val Met Asn Asp Val
        195                 200                 205 gcc aga ggt att gtc aaa gcg gat gtg gca cag agc agc tac ggt ttg    672
Ala Arg Gly Ile Val Lys Ala Asp Val Ala Gln Ser Ser Tyr Gly Leu
    210                 215                 220 tat gga caa ggc cag att gtc gca gtt gcc gat act gga ttg gat aca    720
Tyr Gly Gln Gly Gln Ile Val Ala Val Ala Asp Thr Gly Leu Asp Thr
225                 230                 235                 240 gga aga aac gac agt tcg atg cat gaa gcc ttc cgc ggt aaa ata aca    768
```

```
Gly Arg Asn Asp Ser Ser Met His Glu Ala Phe Arg Gly Lys Ile Thr
                245                 250                 255 gca cta tat gca ctg ggt cgg acg aat aat gcg aat gat acg aac ggt        816
Ala Leu Tyr Ala Leu Gly Arg Thr Asn Asn Ala Asn Asp Thr Asn Gly
            260                 265                 270 cat ggt acc cat gtg gca ggt tcg gta tta gga aat ggc gca acg aat        864
His Gly Thr His Val Ala Gly Ser Val Leu Gly Asn Gly Ala Thr Asn
                275                 280                 285 aaa gga atg gca cct caa gcg aat ctg gtt ttt caa tcc atc atg gat        912
Lys Gly Met Ala Pro Gln Ala Asn Leu Val Phe Gln Ser Ile Met Asp
        290                 295                 300 agc agt ggt ggg ctt gga ggc ttg cct tcc aat ctg caa acc tta ttc        960
Ser Ser Gly Gly Leu Gly Gly Leu Pro Ser Asn Leu Gln Thr Leu Phe
305                 310                 315                 320 agc caa gca ttc agt gca ggt gcc aga att cat aca aac tcc tgg ggg       1008
Ser Gln Ala Phe Ser Ala Gly Ala Arg Ile His Thr Asn Ser Trp Gly
                325                 330                 335 gca gcg gtg aat ggg gcc tac acg aca gat tcc aga aat gtg gat gac       1056
Ala Ala Val Asn Gly Ala Tyr Thr Thr Asp Ser Arg Asn Val Asp Asp
            340                 345                 350 tat gta agg aaa aat gat atg acg att ctt ttc gcg gct ggg aat gaa       1104
Tyr Val Arg Lys Asn Asp Met Thr Ile Leu Phe Ala Ala Gly Asn Glu
        355                 360                 365 agg ccg aac ggc ggt acc atc agt gca cct ggt acg gct aaa aac gcc       1152
Arg Pro Asn Gly Gly Thr Ile Ser Ala Pro Gly Thr Ala Lys Asn Ala
    370                 375                 380 ata aca gtc ggc gca acc gaa aac ctg cgt cca agc ttc ggt tcc tat       1200
Ile Thr Val Gly Ala Thr Glu Asn Leu Arg Pro Ser Phe Gly Ser Tyr
385                 390                 395                 400 gca gat aat att aac cac gtt gca cag ttc tct tcc cgt ggc ccg aca       1248
Ala Asp Asn Ile Asn His Val Ala Gln Phe Ser Ser Arg Gly Pro Thr
                405                 410                 415 aaa gat ggg cga atc aag cct gat gtc atg gcg cca ggg aca tac att       1296
Lys Asp Gly Arg Ile Lys Pro Asp Val Met Ala Pro Gly Thr Tyr Ile
            420                 425                 430 tta tca gca aga tct tct ctt gca ccc gat tcc tcc ttc tgg gcg aat       1344
Leu Ser Ala Arg Ser Ser Leu Ala Pro Asp Ser Ser Phe Trp Ala Asn
        435                 440                 445 cat gac agc aaa tat gcc tat atg ggt gga acg tcc atg gca aca ccg       1392
His Asp Ser Lys Tyr Ala Tyr Met Gly Gly Thr Ser Met Ala Thr Pro
    450                 455                 460 att gtt gcg ggg aat gtt gca cag ctc cgt gag cat ttt gtg aaa aat       1440
Ile Val Ala Gly Asn Val Ala Gln Leu Arg Glu His Phe Val Lys Asn
465                 470                 475                 480 aga gga atc act cct aag cct tcc cta ttg aaa gca gct ttg att gca       1488
Arg Gly Ile Thr Pro Lys Pro Ser Leu Leu Lys Ala Ala Leu Ile Ala
                485                 490                 495 ggt gct gct gat gtt gga ttg ggt tat ccg aac gga aac caa gga tgg       1536
Gly Ala Ala Asp Val Gly Leu Gly Tyr Pro Asn Gly Asn Gln Gly Trp
            500                 505                 510 ggc cga gtg acc ctg gat aaa tcg ttg aac gtt gcc tat gtg aac gaa       1584
Gly Arg Val Thr Leu Asp Lys Ser Leu Asn Val Ala Tyr Val Asn Glu
        515                 520                 525 tcc agt gcc cta tca act agc caa aaa gcg aca tat acc ttt act gca       1632
Ser Ser Ala Leu Ser Thr Ser Gln Lys Ala Thr Tyr Thr Phe Thr Ala
    530                 535                 540 acg gcg ggc aag cca ttg aaa atc tcc ctg gta tgg tcg gat gcc cct       1680
Thr Ala Gly Lys Pro Leu Lys Ile Ser Leu Val Trp Ser Asp Ala Pro
545                 550                 555                 560
```

```
gca agc act act gct tct gta acc ctg gtc aat gat ttg gat ttg gtc   1728
Ala Ser Thr Thr Ala Ser Val Thr Leu Val Asn Asp Leu Asp Leu Val
                565                 570                 575 att aca gca cca aac gga aca aga tat gtc ggg aat gac ttc tca gca   1776
Ile Thr Ala Pro Asn Gly Thr Arg Tyr Val Gly Asn Asp Phe Ser Ala
            580                 585                 590 cca ttt gac aat aac tgg gat ggc cgc aat aac gta gaa aat gta ttt   1824
Pro Phe Asp Asn Asn Trp Asp Gly Arg Asn Asn Val Glu Asn Val Phe
        595                 600                 605 att aat tcg ccc caa agt gga aca tat acc att gag gtg caa gca tat   1872
Ile Asn Ser Pro Gln Ser Gly Thr Tyr Thr Ile Glu Val Gln Ala Tyr
    610                 615                 620 aat gtg ccg gtt gga cca caa aac ttc tcg ttg gca att gtg aac taa   1920
Asn Val Pro Val Gly Pro Gln Asn Phe Ser Leu Ala Ile Val Asn
625                 630                 635

<210> SEQ ID NO 4
<211> LENGTH: 639
<212> TYPE: PRT
<213> ORGANISM: Bacillus sp.

<400> SEQUENCE: 4

Met Arg Lys Lys Val Phe Leu Ser Val Leu Ser Ala Ala Ala Ile
1               5                   10                  15

Leu Ser Thr Val Ala Leu Asn Asn Pro Ser Ala Gly Asp Ala Arg Thr
            20                  25                  30

Phe Asp Leu Asp Phe Lys Gly Ile Gln Thr Thr Thr Asp Val Ser Gly
        35                  40                  45

Phe Ser Lys Gln Arg Gln Thr Gly Ala Ala Ala Phe Leu Val Glu Ser
    50                  55                  60

Glu Asn Val Lys Leu Leu Lys Gly Leu Leu Lys Lys Leu Glu Thr Val
65                  70                  75                  80

Pro Ala Asn Asn Lys Leu His Ile Val Gln Phe Asn Gly Pro Ile Leu
                85                  90                  95

Glu Glu Thr Lys Gln Lys Leu Glu Thr Thr Gly Ala Lys Ile Leu Asp
            100                 105                 110

Tyr Ile Pro Asp Tyr Ala Tyr Ile Val Glu Tyr Glu Gly Asp Val Gln
        115                 120                 125

Ser Lys Val Arg Ser Ile Glu His Val Glu Ser Val Glu Pro Tyr Leu
    130                 135                 140

Pro Lys Tyr Lys Ile Asp Pro Gln Leu Phe Thr Lys Gly Ala Ser Thr
145                 150                 155                 160

Leu Val Lys Ala Leu Ala Leu Asp Thr Lys Gln Asn Asn Lys Glu Val
                165                 170                 175

Gln Leu Arg Gly Ile Glu Glu Ile Ala Gln Tyr Val Ala Ser Asn Asp
            180                 185                 190

Val His Tyr Ile Thr Ala Lys Pro Glu Tyr Lys Val Met Asn Asp Val
        195                 200                 205

Ala Arg Gly Ile Val Lys Ala Asp Val Ala Gln Ser Ser Tyr Gly Leu
    210                 215                 220

Tyr Gly Gln Gly Gln Ile Val Ala Val Ala Asp Thr Gly Leu Asp Thr
225                 230                 235                 240

Gly Arg Asn Asp Ser Ser Met His Glu Ala Phe Arg Gly Lys Ile Thr
                245                 250                 255

Ala Leu Tyr Ala Leu Gly Arg Thr Asn Asn Ala Asn Asp Thr Asn Gly
            260                 265                 270
```

His Gly Thr His Val Ala Gly Ser Val Leu Gly Asn Gly Ala Thr Asn
            275                 280                 285

Lys Gly Met Ala Pro Gln Ala Asn Leu Val Phe Gln Ser Ile Met Asp
        290                 295                 300

Ser Ser Gly Gly Leu Gly Leu Pro Ser Asn Leu Gln Thr Leu Phe
305                 310                 315                 320

Ser Gln Ala Phe Ser Ala Gly Ala Arg Ile His Thr Asn Ser Trp Gly
                325                 330                 335

Ala Ala Val Asn Gly Ala Tyr Thr Thr Asp Ser Arg Asn Val Asp Asp
            340                 345                 350

Tyr Val Arg Lys Asn Asp Met Thr Ile Leu Phe Ala Ala Gly Asn Glu
        355                 360                 365

Arg Pro Asn Gly Gly Thr Ile Ser Ala Pro Gly Thr Ala Lys Asn Ala
    370                 375                 380

Ile Thr Val Gly Ala Thr Glu Asn Leu Arg Pro Ser Phe Gly Ser Tyr
385                 390                 395                 400

Ala Asp Asn Ile Asn His Val Ala Gln Phe Ser Ser Arg Gly Pro Thr
                405                 410                 415

Lys Asp Gly Arg Ile Lys Pro Asp Val Met Ala Pro Gly Thr Tyr Ile
            420                 425                 430

Leu Ser Ala Arg Ser Ser Leu Ala Pro Asp Ser Ser Phe Trp Ala Asn
        435                 440                 445

His Asp Ser Lys Tyr Ala Tyr Met Gly Gly Thr Ser Met Ala Thr Pro
    450                 455                 460

Ile Val Ala Gly Asn Val Ala Gln Leu Arg Glu His Phe Val Lys Asn
465                 470                 475                 480

Arg Gly Ile Thr Pro Lys Pro Ser Leu Leu Lys Ala Ala Leu Ile Ala
                485                 490                 495

Gly Ala Ala Asp Val Gly Leu Gly Tyr Pro Asn Gly Asn Gln Gly Trp
            500                 505                 510

Gly Arg Val Thr Leu Asp Lys Ser Leu Asn Val Ala Tyr Val Asn Glu
        515                 520                 525

Ser Ser Ala Leu Ser Thr Ser Gln Lys Ala Thr Tyr Thr Phe Thr Ala
    530                 535                 540

Thr Ala Gly Lys Pro Leu Lys Ile Ser Leu Val Trp Ser Asp Ala Pro
545                 550                 555                 560

Ala Ser Thr Thr Ala Ser Val Thr Leu Val Asn Asp Leu Asp Leu Val
                565                 570                 575

Ile Thr Ala Pro Asn Gly Thr Arg Tyr Val Gly Asn Asp Phe Ser Ala
            580                 585                 590

Pro Phe Asp Asn Asn Trp Asp Gly Arg Asn Asn Val Glu Asn Val Phe
        595                 600                 605

Ile Asn Ser Pro Gln Ser Gly Thr Tyr Thr Ile Glu Val Gln Ala Tyr
    610                 615                 620

Asn Val Pro Val Gly Pro Gln Asn Phe Ser Leu Ala Ile Val Asn
625                 630                 635

<210> SEQ ID NO 5
<211> LENGTH: 1923
<212> TYPE: DNA
<213> ORGANISM: Bacillus sp.
<220> FEATURE:
<221> NAME/KEY: CDS
<222> LOCATION: (1)..(1923)

<400> SEQUENCE: 5

-continued

| | |
|---|---|
| atg aga aag aag aaa aag gtg ttt tta tct gtt tta tca gct gca gcg<br>Met Arg Lys Lys Lys Lys Val Phe Leu Ser Val Leu Ser Ala Ala Ala<br>1                  5                      10                  15 | 48 |
| att ttg tcg act gtt gcg tta agt aat cca tct gca ggt ggt gca agg<br>Ile Leu Ser Thr Val Ala Leu Ser Asn Pro Ser Ala Gly Gly Ala Arg<br>              20                      25                      30 | 96 |
| aat ttt gat ctg gat ttc aaa gga att cag aca aca act gat gct aaa<br>Asn Phe Asp Leu Asp Phe Lys Gly Ile Gln Thr Thr Thr Asp Ala Lys<br>        35                      40                      45 | 144 |
| ggt ttc tcc aag cag ggg cag act ggt gct gct gct ttt ctg gtg gaa<br>Gly Phe Ser Lys Gln Gly Gln Thr Gly Ala Ala Ala Phe Leu Val Glu<br>    50                      55                      60 | 192 |
| tct gaa aat gtg aaa ctc cca aaa ggt ttg cag aag aag ctt gaa aca<br>Ser Glu Asn Val Lys Leu Pro Lys Gly Leu Gln Lys Lys Leu Glu Thr<br>65                  70                      75                  80 | 240 |
| gtc ccg gca aat aat aaa ctc cat att atc caa ttc aat gga cca att<br>Val Pro Ala Asn Asn Lys Leu His Ile Ile Gln Phe Asn Gly Pro Ile<br>                      85                      90                      95 | 288 |
| tta gaa gaa aca aaa cag cag ctg gaa aaa aca ggg gca aag att ctc<br>Leu Glu Glu Thr Lys Gln Gln Leu Glu Lys Thr Gly Ala Lys Ile Leu<br>            100                    105                    110 | 336 |
| gac tac ata cct gat tat gct tac att gtc gag tat gag ggc gat gtt<br>Asp Tyr Ile Pro Asp Tyr Ala Tyr Ile Val Glu Tyr Glu Gly Asp Val<br>        115                      120                    125 | 384 |
| aag tca gca aca agc acc att gag cac gtg gaa tcc gtg gag cct tat<br>Lys Ser Ala Thr Ser Thr Ile Glu His Val Glu Ser Val Glu Pro Tyr<br>130                    135                    140 | 432 |
| ttg ccg ata tac aga ata gat ccc cag ctt ttc aca aaa ggg gca tca<br>Leu Pro Ile Tyr Arg Ile Asp Pro Gln Leu Phe Thr Lys Gly Ala Ser<br>145                    150                    155                  160 | 480 |
| gag ctt gta aaa gca gtg gcg ctt gat aca aag cag aaa aat aaa gag<br>Glu Leu Val Lys Ala Val Ala Leu Asp Thr Lys Gln Lys Asn Lys Glu<br>                165                    170                    175 | 528 |
| gtg caa tta aga ggc atc gaa caa atc gca caa ttc gca ata agc aat<br>Val Gln Leu Arg Gly Ile Glu Gln Ile Ala Gln Phe Ala Ile Ser Asn<br>            180                    185                    190 | 576 |
| gat gtg cta tat att acg gca aag cct gag tat aag gtg atg aat gat<br>Asp Val Leu Tyr Ile Thr Ala Lys Pro Glu Tyr Lys Val Met Asn Asp<br>        195                      200                    205 | 624 |
| gtt gcg cgt gga att gtc aaa gcg gat gtg gct cag agc agc tac ggg<br>Val Ala Arg Gly Ile Val Lys Ala Asp Val Ala Gln Ser Ser Tyr Gly<br>210                    215                    220 | 672 |
| ttg tat gga caa gga cag atc gta gcg gtt gcc gat aca ggg ctt gat<br>Leu Tyr Gly Gln Gly Gln Ile Val Ala Val Ala Asp Thr Gly Leu Asp<br>225                    230                    235                  240 | 720 |
| aca ggt cgc aat gac agt tcg atg cat gaa gcc ttc cgc ggg aaa att<br>Thr Gly Arg Asn Asp Ser Ser Met His Glu Ala Phe Arg Gly Lys Ile<br>                245                    250                    255 | 768 |
| act gca tta tat gca ttg gga cgg acg aat aat gcc aat gat acg aat<br>Thr Ala Leu Tyr Ala Leu Gly Arg Thr Asn Asn Ala Asn Asp Thr Asn<br>            260                    265                    270 | 816 |
| ggt cat ggt acg cat gtg gct ggc tcc gta tta gga aac ggc tcc act<br>Gly His Gly Thr His Val Ala Gly Ser Val Leu Gly Asn Gly Ser Thr<br>        275                      280                    285 | 864 |
| aat aaa gga atg gcg cct cag gcg aat cta gtc ttc caa tct atc atg<br>Asn Lys Gly Met Ala Pro Gln Ala Asn Leu Val Phe Gln Ser Ile Met<br>290                    295                    300 | 912 |
| gat agc ggt ggg gga ctt gga gga cta cct tcg aat ctg caa acc tta<br>Asp Ser Gly Gly Gly Leu Gly Gly Leu Pro Ser Asn Leu Gln Thr Leu | 960 |

-continued

| | | | | | | | | | | | | | | | | |
|---|---|---|---|---|---|---|---|---|---|---|---|---|---|---|---|---|
| | 305 | | | | 310 | | | | 315 | | | | 320 | | | |
| ttc | agc | caa | gca | tac | agt | gct | ggt | gcc | aga | att | cat | aca | aac | tcc | tgg | 1008 |
| Phe | Ser | Gln | Ala | Tyr | Ser | Ala | Gly | Ala | Arg | Ile | His | Thr | Asn | Ser | Trp | |
| | | | | 325 | | | | | 330 | | | | | 335 | | |
| gga | gca | gca | gtg | aat | ggg | gct | tac | aca | aca | gat | tcc | aga | aat | gtg | gat | 1056 |
| Gly | Ala | Ala | Val | Asn | Gly | Ala | Tyr | Thr | Thr | Asp | Ser | Arg | Asn | Val | Asp | |
| | | | 340 | | | | | 345 | | | | | 350 | | | |
| gac | tat | gtg | cgc | aaa | aat | gat | atg | acg | atc | ctt | ttc | gct | gcc | ggg | aat | 1104 |
| Asp | Tyr | Val | Arg | Lys | Asn | Asp | Met | Thr | Ile | Leu | Phe | Ala | Ala | Gly | Asn | |
| | | 355 | | | | | 360 | | | | | 365 | | | | |
| gaa | gga | ccg | aac | ggc | gga | acc | atc | agt | gca | cca | ggc | aca | gct | aaa | aat | 1152 |
| Glu | Gly | Pro | Asn | Gly | Gly | Thr | Ile | Ser | Ala | Pro | Gly | Thr | Ala | Lys | Asn | |
| | 370 | | | | | 375 | | | | | 380 | | | | | |
| gca | ata | aca | gtc | gga | gct | acg | gaa | aac | ctc | cgc | cca | agc | ttt | ggg | tct | 1200 |
| Ala | Ile | Thr | Val | Gly | Ala | Thr | Glu | Asn | Leu | Arg | Pro | Ser | Phe | Gly | Ser | |
| 385 | | | | | 390 | | | | | 395 | | | | | 400 | |
| tat | gcg | gac | aat | atc | aac | cat | gtg | gca | cag | ttc | tct | tca | cgt | gga | ccg | 1248 |
| Tyr | Ala | Asp | Asn | Ile | Asn | His | Val | Ala | Gln | Phe | Ser | Ser | Arg | Gly | Pro | |
| | | | | 405 | | | | | 410 | | | | | 415 | | |
| aca | aag | gat | gga | cgg | atc | aaa | ccg | gat | gtc | atg | gca | ccg | gga | acg | ttc | 1296 |
| Thr | Lys | Asp | Gly | Arg | Ile | Lys | Pro | Asp | Val | Met | Ala | Pro | Gly | Thr | Phe | |
| | | | 420 | | | | | 425 | | | | | 430 | | | |
| ata | cta | tca | gca | aga | tct | tct | ctt | gca | ccg | gat | tcc | tcc | ttc | tgg | gcg | 1344 |
| Ile | Leu | Ser | Ala | Arg | Ser | Ser | Leu | Ala | Pro | Asp | Ser | Ser | Phe | Trp | Ala | |
| | | 435 | | | | | 440 | | | | | 445 | | | | |
| aac | cat | gac | agt | aaa | tat | gca | tac | atg | ggt | gga | acg | tcc | atg | gct | aca | 1392 |
| Asn | His | Asp | Ser | Lys | Tyr | Ala | Tyr | Met | Gly | Gly | Thr | Ser | Met | Ala | Thr | |
| | 450 | | | | | 455 | | | | | 460 | | | | | |
| ccg | atc | gtt | gct | gga | aac | gtt | gca | cag | ctt | cgt | gag | cat | ttt | gtg | aaa | 1440 |
| Pro | Ile | Val | Ala | Gly | Asn | Val | Ala | Gln | Leu | Arg | Glu | His | Phe | Val | Lys | |
| 465 | | | | | 470 | | | | | 475 | | | | | 480 | |
| aac | aga | ggc | atc | aca | cca | aag | cct | tct | cta | tta | aaa | gcg | gca | ctg | att | 1488 |
| Asn | Arg | Gly | Ile | Thr | Pro | Lys | Pro | Ser | Leu | Leu | Lys | Ala | Ala | Leu | Ile | |
| | | | | 485 | | | | | 490 | | | | | 495 | | |
| gcc | ggt | gca | gct | gac | atc | ggc | ctt | ggc | tac | ccg | aac | ggt | aac | caa | gga | 1536 |
| Ala | Gly | Ala | Ala | Asp | Ile | Gly | Leu | Gly | Tyr | Pro | Asn | Gly | Asn | Gln | Gly | |
| | | | 500 | | | | | 505 | | | | | 510 | | | |
| tgg | gga | cga | gtg | aca | ttg | gat | aaa | tcc | ctg | aac | gtt | gcc | tat | gtg | aac | 1584 |
| Trp | Gly | Arg | Val | Thr | Leu | Asp | Lys | Ser | Leu | Asn | Val | Ala | Tyr | Val | Asn | |
| | | 515 | | | | | 520 | | | | | 525 | | | | |
| gag | tcc | agt | tct | cta | tcc | acc | agc | caa | aaa | gcg | acg | tac | tcg | ttt | act | 1632 |
| Glu | Ser | Ser | Ser | Leu | Ser | Thr | Ser | Gln | Lys | Ala | Thr | Tyr | Ser | Phe | Thr | |
| | 530 | | | | | 535 | | | | | 540 | | | | | |
| gct | act | gcc | ggc | aag | cct | ttg | aaa | atc | tcc | ctg | gta | tgg | tct | gat | gcc | 1680 |
| Ala | Thr | Ala | Gly | Lys | Pro | Leu | Lys | Ile | Ser | Leu | Val | Trp | Ser | Asp | Ala | |
| 545 | | | | | 550 | | | | | 555 | | | | | 560 | |
| cct | gcg | agc | aca | act | gct | tcc | gta | acg | ctt | gtc | aat | gat | ctg | gac | ctt | 1728 |
| Pro | Ala | Ser | Thr | Thr | Ala | Ser | Val | Thr | Leu | Val | Asn | Asp | Leu | Asp | Leu | |
| | | | | 565 | | | | | 570 | | | | | 575 | | |
| gtc | att | acc | gct | cca | aat | gga | aca | cag | tat | gta | gga | aat | gac | ttt | act | 1776 |
| Val | Ile | Thr | Ala | Pro | Asn | Gly | Thr | Gln | Tyr | Val | Gly | Asn | Asp | Phe | Thr | |
| | | | 580 | | | | | 585 | | | | | 590 | | | |
| tcg | cca | tac | aat | gat | aac | tgg | gat | ggc | cgc | aat | aac | gta | gaa | aat | gta | 1824 |
| Ser | Pro | Tyr | Asn | Asp | Asn | Trp | Asp | Gly | Arg | Asn | Asn | Val | Glu | Asn | Val | |
| | | 595 | | | | | 600 | | | | | 605 | | | | |
| ttt | att | aat | gca | cca | caa | agc | ggg | acg | tat | aca | att | gag | gta | cag | gct | 1872 |
| Phe | Ile | Asn | Ala | Pro | Gln | Ser | Gly | Thr | Tyr | Thr | Ile | Glu | Val | Gln | Ala | |
| | 610 | | | | | 615 | | | | | 620 | | | | | |
| tat | aac | gta | ccg | gtt | gga | cca | cag | acc | ttc | tcg | ttg | gca | att | gtg | aat | 1920 |

-continued

Tyr Asn Val Pro Val Gly Pro Gln Thr Phe Ser Leu Ala Ile Val Asn
625                 630                 635                 640 taa                                                                    1923

<210> SEQ ID NO 6
<211> LENGTH: 640
<212> TYPE: PRT
<213> ORGANISM: Bacillus sp.

<400> SEQUENCE: 6

Met Arg Lys Lys Lys Val Phe Leu Ser Val Leu Ser Ala Ala Ala Ala
1               5                   10                  15

Ile Leu Ser Thr Val Ala Leu Ser Asn Pro Ser Ala Gly Gly Ala Arg
                20                  25                  30

Asn Phe Asp Leu Asp Phe Lys Gly Ile Gln Thr Thr Asp Ala Lys
            35                  40                  45

Gly Phe Ser Lys Gln Gly Gln Thr Gly Ala Ala Phe Leu Val Glu
        50                  55                  60

Ser Glu Asn Val Lys Leu Pro Lys Gly Leu Gln Lys Leu Glu Thr
65                  70                  75                  80

Val Pro Ala Asn Asn Lys Leu His Ile Ile Gln Phe Asn Gly Pro Ile
                85                  90                  95

Leu Glu Glu Thr Lys Gln Gln Leu Glu Lys Thr Gly Ala Lys Ile Leu
            100                 105                 110

Asp Tyr Ile Pro Asp Tyr Ala Tyr Ile Val Glu Tyr Glu Gly Asp Val
        115                 120                 125

Lys Ser Ala Thr Ser Thr Ile Glu His Val Glu Ser Val Glu Pro Tyr
130                 135                 140

Leu Pro Ile Tyr Arg Ile Asp Pro Gln Leu Phe Thr Lys Gly Ala Ser
145                 150                 155                 160

Glu Leu Val Lys Ala Val Ala Leu Asp Thr Lys Gln Lys Asn Lys Glu
                165                 170                 175

Val Gln Leu Arg Gly Ile Glu Gln Ile Ala Gln Phe Ala Ile Ser Asn
            180                 185                 190

Asp Val Leu Tyr Ile Thr Ala Lys Pro Glu Tyr Lys Val Met Asn Asp
        195                 200                 205

Val Ala Arg Gly Ile Val Lys Ala Asp Val Ala Gln Ser Ser Tyr Gly
210                 215                 220

Leu Tyr Gly Gln Gly Gln Ile Val Ala Val Ala Asp Thr Gly Leu Asp
225                 230                 235                 240

Thr Gly Arg Asn Asp Ser Ser Met His Glu Ala Phe Arg Gly Lys Ile
                245                 250                 255

Thr Ala Leu Tyr Ala Leu Gly Arg Thr Asn Asn Ala Asn Asp Thr Asn
            260                 265                 270

Gly His Gly Thr His Val Ala Gly Ser Val Leu Gly Asn Gly Ser Thr
        275                 280                 285

Asn Lys Gly Met Ala Pro Gln Ala Asn Leu Val Phe Gln Ser Ile Met
290                 295                 300

Asp Ser Gly Gly Gly Leu Gly Gly Leu Pro Ser Asn Leu Gln Thr Leu
305                 310                 315                 320

Phe Ser Gln Ala Tyr Ser Ala Gly Ala Arg Ile His Thr Asn Ser Trp
                325                 330                 335

Gly Ala Ala Val Asn Gly Ala Tyr Thr Thr Asp Ser Arg Asn Val Asp
            340                 345                 350

-continued

```
Asp Tyr Val Arg Lys Asn Asp Met Thr Ile Leu Phe Ala Ala Gly Asn
        355                 360                 365

Glu Gly Pro Asn Gly Gly Thr Ile Ser Ala Pro Gly Thr Ala Lys Asn
    370                 375                 380

Ala Ile Thr Val Gly Ala Thr Glu Asn Leu Arg Pro Ser Phe Gly Ser
385                 390                 395                 400

Tyr Ala Asp Asn Ile Asn His Val Ala Gln Phe Ser Ser Arg Gly Pro
                405                 410                 415

Thr Lys Asp Gly Arg Ile Lys Pro Asp Val Met Ala Pro Gly Thr Phe
            420                 425                 430

Ile Leu Ser Ala Arg Ser Ser Leu Ala Pro Asp Ser Ser Phe Trp Ala
            435                 440                 445

Asn His Asp Ser Lys Tyr Ala Tyr Met Gly Gly Thr Ser Met Ala Thr
    450                 455                 460

Pro Ile Val Ala Gly Asn Val Ala Gln Leu Arg Glu His Phe Val Lys
465                 470                 475                 480

Asn Arg Gly Ile Thr Pro Lys Pro Ser Leu Leu Lys Ala Ala Leu Ile
                485                 490                 495

Ala Gly Ala Ala Asp Ile Gly Leu Gly Tyr Pro Asn Gly Asn Gln Gly
            500                 505                 510

Trp Gly Arg Val Thr Leu Asp Lys Ser Leu Asn Val Ala Tyr Val Asn
        515                 520                 525

Glu Ser Ser Leu Ser Thr Ser Gln Lys Ala Thr Tyr Ser Phe Thr
    530                 535                 540

Ala Thr Ala Gly Lys Pro Leu Lys Ile Ser Leu Val Trp Ser Asp Ala
545                 550                 555                 560

Pro Ala Ser Thr Thr Ala Ser Val Thr Leu Val Asn Asp Leu Asp Leu
                565                 570                 575

Val Ile Thr Ala Pro Asn Gly Thr Gln Tyr Val Gly Asn Asp Phe Thr
            580                 585                 590

Ser Pro Tyr Asn Asp Asn Trp Asp Gly Arg Asn Asn Val Glu Asn Val
        595                 600                 605

Phe Ile Asn Ala Pro Gln Ser Gly Thr Tyr Thr Ile Glu Val Gln Ala
    610                 615                 620

Tyr Asn Val Pro Val Gly Pro Gln Thr Phe Ser Leu Ala Ile Val Asn
625                 630                 635                 640

<210> SEQ ID NO 7
<211> LENGTH: 1923
<212> TYPE: DNA
<213> ORGANISM: Bacillus sp.
<220> FEATURE:
<221> NAME/KEY: CDS
<222> LOCATION: (1)..(1923)

<400> SEQUENCE: 7 atg aga aag aag aaa aag gtg ttt tta tct gtt tta tca gct gca gcg      48
Met Arg Lys Lys Lys Lys Val Phe Leu Ser Val Leu Ser Ala Ala Ala
1               5                   10                  15 att ttg tcg act gtt gcg tta agt aat cca tct gca ggt ggt gca agg      96
Ile Leu Ser Thr Val Ala Leu Ser Asn Pro Ser Ala Gly Gly Ala Arg
                20                  25                  30 aat ttt gat ctg gat ttc aaa gga att cag aca aca act gat gct aaa     144
Asn Phe Asp Leu Asp Phe Lys Gly Ile Gln Thr Thr Thr Asp Ala Lys
            35                  40                  45 ggt ttc tcc aag cag ggg cag act ggt gct gct gct ttt ctg gtg gaa     192
Gly Phe Ser Lys Gln Gly Gln Thr Gly Ala Ala Ala Phe Leu Val Glu
```

```
            50                  55                  60
tct gaa aat gtg aaa ctc cca aaa ggt ttg cag aag aag ctt gaa aca      240
Ser Glu Asn Val Lys Leu Pro Lys Gly Leu Gln Lys Lys Leu Glu Thr
 65              70                  75                  80 gtc ccg gca aat aat aaa ctc cat att atc caa ttc aat gga cca att      288
Val Pro Ala Asn Asn Lys Leu His Ile Ile Gln Phe Asn Gly Pro Ile
                 85                  90                  95 tta gaa gaa aca aaa cag cag ctg gaa aaa aca ggg gca aag att ctc      336
Leu Glu Glu Thr Lys Gln Gln Leu Glu Lys Thr Gly Ala Lys Ile Leu
            100                 105                 110 gac tac ata cct gat tat gct tac att gtc gag tat gag ggc gat gtt      384
Asp Tyr Ile Pro Asp Tyr Ala Tyr Ile Val Glu Tyr Glu Gly Asp Val
        115                 120                 125 aag tca gca aca agc acc att gag cac gtg gaa tcc gtg gag cct tat      432
Lys Ser Ala Thr Ser Thr Ile Glu His Val Glu Ser Val Glu Pro Tyr
    130                 135                 140 ttg ccg ata tac aga ata gat ccc cag ctt ttc aca aaa ggg gca tca      480
Leu Pro Ile Tyr Arg Ile Asp Pro Gln Leu Phe Thr Lys Gly Ala Ser
145                 150                 155                 160 gag ctt gta aaa gca gtg gcg ctt gat aca aag cag aaa aat aaa gag      528
Glu Leu Val Lys Ala Val Ala Leu Asp Thr Lys Gln Lys Asn Lys Glu
                165                 170                 175 gtg caa tta aga ggc atc gaa caa atc gca caa ttc gca ata agc aat      576
Val Gln Leu Arg Gly Ile Glu Gln Ile Ala Gln Phe Ala Ile Ser Asn
            180                 185                 190 gat gtg cta tat att acg gca aag cct gag tat aag gtg atg aat gat      624
Asp Val Leu Tyr Ile Thr Ala Lys Pro Glu Tyr Lys Val Met Asn Asp
        195                 200                 205 gtt gcg cgt gga att gtc aaa gcg gat gtg gct cag agc agc tac ggg      672
Val Ala Arg Gly Ile Val Lys Ala Asp Val Ala Gln Ser Ser Tyr Gly
    210                 215                 220 ttg tat gga caa gga cag atc gta gcg gtt gcc gat aca ggg ctt gat      720
Leu Tyr Gly Gln Gly Gln Ile Val Ala Val Ala Asp Thr Gly Leu Asp
225                 230                 235                 240 aca ggt cgc aat gac agt tcg atg cat gaa gcc ttc cgc ggg aaa att      768
Thr Gly Arg Asn Asp Ser Ser Met His Glu Ala Phe Arg Gly Lys Ile
                245                 250                 255 act gca tta tat gca ttg gga cgg acg aat aat gcc aat gat acg aat      816
Thr Ala Leu Tyr Ala Leu Gly Arg Thr Asn Asn Ala Asn Asp Thr Asn
            260                 265                 270 ggt cat ggt acg cat gtg gct ggc tcc gta tta gga aac ggc tcc act      864
Gly His Gly Thr His Val Ala Gly Ser Val Leu Gly Asn Gly Ser Thr
        275                 280                 285 aat aaa gga atg gcg cct cag gcg aat cta gtc ttc caa tct atc atg      912
Asn Lys Gly Met Ala Pro Gln Ala Asn Leu Val Phe Gln Ser Ile Met
    290                 295                 300 gat agc ggt ggg gga ctt gga gga cta cct tcg aat ctg caa acc tta      960
Asp Ser Gly Gly Gly Leu Gly Gly Leu Pro Ser Asn Leu Gln Thr Leu
305                 310                 315                 320 ttc agc caa gca tac agt gct ggt gcc aga att cat aca aac tcc tgg      1008
Phe Ser Gln Ala Tyr Ser Ala Gly Ala Arg Ile His Thr Asn Ser Trp
                325                 330                 335 gga gca gca gtg aat ggg gct tac aca aca gat tcc aga aat gtg gat      1056
Gly Ala Ala Val Asn Gly Ala Tyr Thr Thr Asp Ser Arg Asn Val Asp
            340                 345                 350 gac tat gtg cgc aaa aat gat atg acg atc ctt ttc gct gcc ggg aat      1104
Asp Tyr Val Arg Lys Asn Asp Met Thr Ile Leu Phe Ala Ala Gly Asn
        355                 360                 365 gaa gga ccg aac ggc gga acc atc agt gca cca ggc aca gct aaa aat      1152
```

```
        Glu Gly Pro Asn Gly Gly Thr Ile Ser Ala Pro Gly Thr Ala Lys Asn
            370                 375                 380 gca ata aca gtc gga gct acg gaa aac ctc cgc cca agc ttt ggg tct      1200
Ala Ile Thr Val Gly Ala Thr Glu Asn Leu Arg Pro Ser Phe Gly Ser
385                 390                 395                 400 tat gcg gac aat atc aac cat gtg gca cag ttc tct tca cgt gga ccg      1248
Tyr Ala Asp Asn Ile Asn His Val Ala Gln Phe Ser Ser Arg Gly Pro
                405                 410                 415 aca aag gat gga cgg atc aaa ccg gat gtc atg gca ccg gga acg ttc      1296
Thr Lys Asp Gly Arg Ile Lys Pro Asp Val Met Ala Pro Gly Thr Phe
            420                 425                 430 ata cta tca gca aga tct tct ctt gca ccg gat tcc tcc ttc tgg gcg      1344
Ile Leu Ser Ala Arg Ser Ser Leu Ala Pro Asp Ser Ser Phe Trp Ala
        435                 440                 445 aac cat gac agt aaa tat gca tac atg ggt gga acg tcc atg gct aca      1392
Asn His Asp Ser Lys Tyr Ala Tyr Met Gly Gly Thr Ser Met Ala Thr
    450                 455                 460 ccg atc gtt gct gga aac gtg gca cag ctt cgt gag cat ttt gtg aaa      1440
Pro Ile Val Ala Gly Asn Val Ala Gln Leu Arg Glu His Phe Val Lys
465                 470                 475                 480 aac aga ggc atc aca cca aag cct tct cta tta aaa gcg gca ctg att      1488
Asn Arg Gly Ile Thr Pro Lys Pro Ser Leu Leu Lys Ala Ala Leu Ile
                485                 490                 495 gcc ggt gca gct gac atc ggc ctt ggc tac ccg aac ggt aac caa gga      1536
Ala Gly Ala Ala Asp Ile Gly Leu Gly Tyr Pro Asn Gly Asn Gln Gly
            500                 505                 510 tgg gga cga gtg aca ttg gat aaa tcc ctg aac gtt gcc tat gtg aac      1584
Trp Gly Arg Val Thr Leu Asp Lys Ser Leu Asn Val Ala Tyr Val Asn
        515                 520                 525 gag tcc agt tct cta tcc acc agc caa aaa gcg acg tac tcg ttt act      1632
Glu Ser Ser Ser Leu Ser Thr Ser Gln Lys Ala Thr Tyr Ser Phe Thr
    530                 535                 540 gct act gcc ggc aag cct ttg aaa atc tcc ctg gta tgg tct gat gcc      1680
Ala Thr Ala Gly Lys Pro Leu Lys Ile Ser Leu Val Trp Ser Asp Ala
545                 550                 555                 560 cct gcg agc aca act gct tcc gta acg ctt gtc aat gat ctg gac ctt      1728
Pro Ala Ser Thr Thr Ala Ser Val Thr Leu Val Asn Asp Leu Asp Leu
                565                 570                 575 gtc att acc gct cca aat gga aca cag tat gta gga aat gac ttt act      1776
Val Ile Thr Ala Pro Asn Gly Thr Gln Tyr Val Gly Asn Asp Phe Thr
            580                 585                 590 tcg cca tac aat gat aac tgg gat ggc cgc aat aac gta gaa aat gta      1824
Ser Pro Tyr Asn Asp Asn Trp Asp Gly Arg Asn Asn Val Glu Asn Val
        595                 600                 605 ttt att aat gca cca caa agc ggg acg tat aca att gaa gta cag gct      1872
Phe Ile Asn Ala Pro Gln Ser Gly Thr Tyr Thr Ile Glu Val Gln Ala
    610                 615                 620 tat aac gta ccg gtt gga cca cag aac ttc tcg ttg gca att gtg aat      1920
Tyr Asn Val Pro Val Gly Pro Gln Asn Phe Ser Leu Ala Ile Val Asn
625                 630                 635                 640 taa                                                                  1923

<210> SEQ ID NO 8
<211> LENGTH: 640
<212> TYPE: PRT
<213> ORGANISM: Bacillus sp.

<400> SEQUENCE: 8

Met Arg Lys Lys Lys Val Phe Leu Ser Val Leu Ser Ala Ala Ala
1               5                   10                  15
```

```
Ile Leu Ser Thr Val Ala Leu Ser Asn Pro Ser Ala Gly Gly Ala Arg
            20                  25                  30

Asn Phe Asp Leu Asp Phe Lys Gly Ile Gln Thr Thr Thr Asp Ala Lys
            35                  40                  45

Gly Phe Ser Lys Gln Gly Gln Thr Gly Ala Ala Phe Leu Val Glu
    50                  55                  60

Ser Glu Asn Val Lys Leu Pro Lys Gly Leu Gln Lys Lys Leu Glu Thr
65                  70                  75                  80

Val Pro Ala Asn Asn Lys Leu His Ile Ile Gln Phe Asn Gly Pro Ile
                85                  90                  95

Leu Glu Glu Thr Lys Gln Gln Leu Glu Lys Thr Gly Ala Lys Ile Leu
            100                 105                 110

Asp Tyr Ile Pro Asp Tyr Ala Tyr Ile Val Glu Tyr Glu Gly Asp Val
            115                 120                 125

Lys Ser Ala Thr Ser Thr Ile Glu His Val Glu Ser Val Glu Pro Tyr
130                 135                 140

Leu Pro Ile Tyr Arg Ile Asp Pro Gln Leu Phe Thr Lys Gly Ala Ser
145                 150                 155                 160

Glu Leu Val Lys Ala Val Ala Leu Asp Thr Lys Gln Lys Asn Lys Glu
                165                 170                 175

Val Gln Leu Arg Gly Ile Glu Gln Ile Ala Gln Phe Ala Ile Ser Asn
            180                 185                 190

Asp Val Leu Tyr Ile Thr Ala Lys Pro Glu Tyr Lys Val Met Asn Asp
            195                 200                 205

Val Ala Arg Gly Ile Val Lys Ala Asp Val Ala Gln Ser Ser Tyr Gly
            210                 215                 220

Leu Tyr Gly Gln Gly Gln Ile Val Ala Val Ala Asp Thr Gly Leu Asp
225                 230                 235                 240

Thr Gly Arg Asn Asp Ser Ser Met His Glu Ala Phe Arg Gly Lys Ile
                245                 250                 255

Thr Ala Leu Tyr Ala Leu Gly Arg Thr Asn Asn Ala Asn Asp Thr Asn
            260                 265                 270

Gly His Gly Thr His Val Ala Gly Ser Val Leu Gly Asn Gly Ser Thr
            275                 280                 285

Asn Lys Gly Met Ala Pro Gln Ala Asn Leu Val Phe Gln Ser Ile Met
290                 295                 300

Asp Ser Gly Gly Gly Leu Gly Gly Leu Pro Ser Asn Leu Gln Thr Leu
305                 310                 315                 320

Phe Ser Gln Ala Tyr Ser Ala Gly Ala Arg Ile His Thr Asn Ser Trp
                325                 330                 335

Gly Ala Ala Val Asn Gly Ala Tyr Thr Thr Asp Ser Arg Asn Val Asp
            340                 345                 350

Asp Tyr Val Arg Lys Asn Asp Met Thr Ile Leu Phe Ala Ala Gly Asn
            355                 360                 365

Glu Gly Pro Asn Gly Gly Thr Ile Ser Ala Pro Gly Thr Ala Lys Asn
    370                 375                 380

Ala Ile Thr Val Gly Ala Thr Glu Asn Leu Arg Pro Ser Phe Gly Ser
385                 390                 395                 400

Tyr Ala Asp Asn Ile Asn His Val Ala Gln Phe Ser Ser Arg Gly Pro
                405                 410                 415

Thr Lys Asp Gly Arg Ile Lys Pro Asp Val Met Ala Pro Gly Thr Phe
            420                 425                 430
```

-continued

```
Ile Leu Ser Ala Arg Ser Ser Leu Ala Pro Asp Ser Ser Phe Trp Ala
        435                 440                 445

Asn His Asp Ser Lys Tyr Ala Tyr Met Gly Gly Thr Ser Met Ala Thr
        450                 455                 460

Pro Ile Val Ala Gly Asn Val Ala Gln Leu Arg Glu His Phe Val Lys
465                 470                 475                 480

Asn Arg Gly Ile Thr Pro Lys Pro Ser Leu Leu Lys Ala Ala Leu Ile
                485                 490                 495

Ala Gly Ala Ala Asp Ile Gly Leu Gly Tyr Pro Asn Gly Asn Gln Gly
            500                 505                 510

Trp Gly Arg Val Thr Leu Asp Lys Ser Leu Asn Val Ala Tyr Val Asn
        515                 520                 525

Glu Ser Ser Ser Leu Ser Thr Ser Gln Lys Ala Thr Tyr Ser Phe Thr
        530                 535                 540

Ala Thr Ala Gly Lys Pro Leu Lys Ile Ser Leu Val Trp Ser Asp Ala
545                 550                 555                 560

Pro Ala Ser Thr Thr Ala Ser Val Thr Leu Val Asn Asp Leu Asp Leu
                565                 570                 575

Val Ile Thr Ala Pro Asn Gly Thr Gln Tyr Val Gly Asn Asp Phe Thr
            580                 585                 590

Ser Pro Tyr Asn Asp Asn Trp Asp Gly Arg Asn Asn Val Glu Asn Val
        595                 600                 605

Phe Ile Asn Ala Pro Gln Ser Gly Thr Tyr Thr Ile Glu Val Gln Ala
        610                 615                 620

Tyr Asn Val Pro Val Gly Pro Gln Asn Phe Ser Leu Ala Ile Val Asn
625                 630                 635                 640

<210> SEQ ID NO 9
<211> LENGTH: 20
<212> TYPE: PRT
<213> ORGANISM: Bacillus sp.

<400> SEQUENCE: 9

Asn Asp Val Ala Arg His Ile Val Lys Ala Asp Val Ala Gln Ser Ser
1               5                   10                  15

Tyr Gly Leu Tyr
            20

<210> SEQ ID NO 10
<211> LENGTH: 14
<212> TYPE: PRT
<213> ORGANISM: Bacillus sp.

<400> SEQUENCE: 10

Gly Ile Val Lys Ala Asp Val Ala Gln Ser Ser Tyr Gly Leu
1               5                   10

<210> SEQ ID NO 11
<211> LENGTH: 13
<212> TYPE: PRT
<213> ORGANISM: Bacillus sp.

<400> SEQUENCE: 11

Ile Lys Pro Asp Val Met Ala Pro Gly Thr Tyr Ile Leu
1               5                   10

<210> SEQ ID NO 12
<211> LENGTH: 20
<212> TYPE: PRT
```

<213> ORGANISM: Bacillus sp.

<400> SEQUENCE: 12

Asn Ala Ile Thr Val Gly Ala Thr Glu Asn Leu Arg Pro Ser Phe Gly
1               5                   10                  15

Ser Tyr Ala Asp
            20

<210> SEQ ID NO 13
<211> LENGTH: 16
<212> TYPE: PRT
<213> ORGANISM: Bacillus sp.

<400> SEQUENCE: 13

Lys Asn Asp Met Val Ile Leu Phe Ala Ala Gly Asn Glu Gly Pro Asn
1               5                   10                  15

<210> SEQ ID NO 14
<211> LENGTH: 24
<212> TYPE: DNA
<213> ORGANISM: Artificial Sequence
<220> FEATURE:
<221> NAME/KEY: misc_feature
<222> LOCATION: ()..()
<223> OTHER INFORMATION: Description of Artificial Sequence: primer
<221> NAME/KEY: misc_feature
<222> LOCATION: (6)..(6)
<223> OTHER INFORMATION: n is a, g, c or t
<221> NAME/KEY: misc_feature
<222> LOCATION: (12)..(12)
<223> OTHER INFORMATION: n is a, g, c or t
<221> NAME/KEY: misc_feature
<222> LOCATION: (18)..(18)
<223> OTHER INFORMATION: n is a, g, c or t
<221> NAME/KEY: misc_feature
<222> LOCATION: (21)..(21)
<223> OTHER INFORMATION: n is a, g, c or t

<400> SEQUENCE: 14
athgtnaarg cngaygtngc ncar                                          24

<210> SEQ ID NO 15
<211> LENGTH: 23
<212> TYPE: DNA
<213> ORGANISM: Artificial Sequence
<220> FEATURE:
<221> NAME/KEY: misc_feature
<222> LOCATION: ()..()
<223> OTHER INFORMATION: Description of Artificial Sequence: primer
<221> NAME/KEY: misc_feature
<222> LOCATION: (9)..(9)
<223> OTHER INFORMATION: n is a, g, c or t
<221> NAME/KEY: misc_feature
<222> LOCATION: (15)..(15)
<223> OTHER INFORMATION: n is a, g, c or t
<221> NAME/KEY: misc_feature
<222> LOCATION: (21)..(21)
<223> OTHER INFORMATION: n is a, g, c or t

<400> SEQUENCE: 15
tadttyggnc trcantaccg ngg                                           23

<210> SEQ ID NO 16
<211> LENGTH: 23
<212> TYPE: DNA
<213> ORGANISM: Artificial Sequence
<220> FEATURE:
<221> NAME/KEY: misc_feature
<222> LOCATION: ()..()
<223> OTHER INFORMATION: Description of Artificial Sequence: primer

```
<221> NAME/KEY: misc_feature
<222> LOCATION: (9)..(9)
<223> OTHER INFORMATION: n is a, g, c or t
<221> NAME/KEY: misc_feature
<222> LOCATION: (15)..(15)
<223> OTHER INFORMATION: n is a, g, c or t
<221> NAME/KEY: misc_feature
<222> LOCATION: (21)..(21)
<223> OTHER INFORMATION: n is a, g, c or t

<400> SEQUENCE: 16
athaarccng aygtnatggc ncc                                              23

<210> SEQ ID NO 17
<211> LENGTH: 24
<212> TYPE: DNA
<213> ORGANISM: Artificial Sequence
<220> FEATURE:
<221> NAME/KEY: misc_feature
<222> LOCATION: ()..()
<223> OTHER INFORMATION: Description of Artificial Sequence: primer
<221> NAME/KEY: misc_feature
<222> LOCATION: (6)..(6)
<223> OTHER INFORMATION: n is a, g, c or t
<221> NAME/KEY: misc_feature
<222> LOCATION: (12)..(12)
<223> OTHER INFORMATION: n is a, g, c or t
<221> NAME/KEY: misc_feature
<222> LOCATION: (15)..(15)
<223> OTHER INFORMATION: n is a, g, c or t
<221> NAME/KEY: misc_feature
<222> LOCATION: (18)..(18)
<223> OTHER INFORMATION: n is a, g, c or t
<221> NAME/KEY: misc_feature
<222> LOCATION: (21)..(21)
<223> OTHER INFORMATION: n is a, g, c or t
<221> NAME/KEY: misc_feature
<222> LOCATION: (24)..(24)
<223> OTHER INFORMATION: n is a, g, c or t

<400> SEQUENCE: 17
ttrcgntadt gncanccncg ntgn                                             24

<210> SEQ ID NO 18
<211> LENGTH: 23
<212> TYPE: DNA
<213> ORGANISM: Artificial Sequence
<220> FEATURE:
<221> NAME/KEY: misc_feature
<222> LOCATION: ()..()
<223> OTHER INFORMATION: Description of Artificial Sequence: primer
<221> NAME/KEY: misc_feature
<222> LOCATION: (6)..(6)
<223> OTHER INFORMATION: n is a, g, c or t
<221> NAME/KEY: misc_feature
<222> LOCATION: (9)..(9)
<223> OTHER INFORMATION: n is a, g, c or t
<221> NAME/KEY: misc_feature
<222> LOCATION: (12)..(12)
<223> OTHER INFORMATION: n is a, g, c or t
<221> NAME/KEY: misc_feature
<222> LOCATION: (15)..(15)
<223> OTHER INFORMATION: n is a, g, c or t
<221> NAME/KEY: misc_feature
<222> LOCATION: (18)..(18)
<223> OTHER INFORMATION: n is a, g, c or t

<400> SEQUENCE: 18
athacngtng gngcnacnga raa                                              23

<210> SEQ ID NO 19
<211> LENGTH: 23
<212> TYPE: DNA
```

```
<213> ORGANISM: Artificial Sequence
<220> FEATURE:
<221> NAME/KEY: misc_feature
<222> LOCATION: ()..()
<223> OTHER INFORMATION: Description of Artificial Sequence: primer
<221> NAME/KEY: misc_feature
<222> LOCATION: (12)..(12)
<223> OTHER INFORMATION: n is a, g, c or t
<221> NAME/KEY: misc_feature
<222> LOCATION: (18)..(18)
<223> OTHER INFORMATION: n is a, g, c or t

<400> SEQUENCE: 19
ttrctrtacc antadranaa rcg                                            23

<210> SEQ ID NO 20
<211> LENGTH: 23
<212> TYPE: DNA
<213> ORGANISM: Artificial Sequence
<220> FEATURE:
<221> NAME/KEY: misc_feature
<222> LOCATION: ()..()
<223> OTHER INFORMATION: Description of Artificial Sequence: primer
<221> NAME/KEY: misc_feature
<222> LOCATION: (12)..(12)
<223> OTHER INFORMATION: n is a, g, c or t
<221> NAME/KEY: misc_feature
<222> LOCATION: (18)..(18)
<223> OTHER INFORMATION: n is a, g, c or t

<400> SEQUENCE: 20
aaygayatgg tnatgytntt ygc                                            23

<210> SEQ ID NO 21
<211> LENGTH: 21
<212> TYPE: DNA
<213> ORGANISM: Artificial Sequence
<220> FEATURE:
<221> NAME/KEY: misc_feature
<222> LOCATION: ()..()
<223> OTHER INFORMATION: Description of Artificial Sequence: primer

<400> SEQUENCE: 21
tcggcaactg cgacaatctg g                                              21

<210> SEQ ID NO 22
<211> LENGTH: 21
<212> TYPE: DNA
<213> ORGANISM: Artificial Sequence
<220> FEATURE:
<221> NAME/KEY: misc_feature
<222> LOCATION: ()..()
<223> OTHER INFORMATION: Description of Artificial Sequence: primer

<400> SEQUENCE: 22
tctggaatct gtcgtgtagg c                                              21

<210> SEQ ID NO 23
<211> LENGTH: 20
<212> TYPE: DNA
<213> ORGANISM: Artificial Sequence
<220> FEATURE:
<221> NAME/KEY: misc_feature
<222> LOCATION: ()..()
<223> OTHER INFORMATION: Description of Artificial Sequence: primer

<400> SEQUENCE: 23
aacggcggta ccatcagtgc                                                20
```

-continued

```
<210> SEQ ID NO 24
<211> LENGTH: 21
<212> TYPE: DNA
<213> ORGANISM: Artificial Sequence
<220> FEATURE:
<221> NAME/KEY: misc_feature
<222> LOCATION: ()..()
<223> OTHER INFORMATION: Description of Artificial Sequence: primer

<400> SEQUENCE: 24
ggaggcttgc cttccaatct g                                            21
```